(12) United States Patent
Negami et al.

(10) Patent No.: US 6,507,402 B2
(45) Date of Patent: Jan. 14, 2003

(54) SPR SENSOR PLATE AND IMMUNE REACTION MEASURING INSTRUMENT USING THE SAME

(75) Inventors: Mitsuhiro Negami, Shizuoka (JP); Muneaki Nakamura, Shizuoka (JP)

(73) Assignee: Suzuki Motor Corporation, Shizuoka (JP)

( * ) Notice: Subject to any disclaimer, the term of this patent is extended or adjusted under 35 U.S.C. 154(b) by 4 days.

(21) Appl. No.: 09/899,164

(22) Filed: Jul. 6, 2001

(65) Prior Publication Data

US 2002/0005953 A1 Jan. 17, 2002

(30) Foreign Application Priority Data

Jul. 11, 2000 (JP) ........................................ 2000-210024

(51) Int. Cl.[7] ............................................... G01N 21/55
(52) U.S. Cl. ........................................................ 356/445
(58) Field of Search .......................................... 356/445

(56) References Cited

U.S. PATENT DOCUMENTS

| | | | |
|---|---|---|---|
| 4,886,357 A | | 12/1989 | Harrick |
| 5,047,213 A | * | 9/1991 | Finlan et al. ............ 422/82.11 |
| 5,485,277 A | * | 1/1996 | Foster ........................ 356/445 |
| 5,815,278 A | | 9/1998 | Johnston et al. |
| 5,822,073 A | | 10/1998 | Yee et al. |
| 5,898,503 A | * | 4/1999 | Keller et al. ................ 356/445 |
| 5,926,284 A | * | 7/1999 | Naya et al. ................. 356/445 |
| 5,991,048 A | | 11/1999 | Karlson et al. |
| 6,111,652 A | * | 8/2000 | Melendez et al. .......... 356/445 |

FOREIGN PATENT DOCUMENTS

| | | |
|---|---|---|
| EP | 0797091 | 9/1997 |
| EP | 0834735 | 4/1998 |
| WO | 95/22754 | 8/1995 |

* cited by examiner

Primary Examiner—Stephone B. Allen
Assistant Examiner—Eric Spears
(74) Attorney, Agent, or Firm—Greenblum & Bernstein, P.L.C.

(57) ABSTRACT

To provide an SPR sensor plate which allows easy fixation of an antibody and easy retention of a subject and which can be manufactured easily, as well as an immune reaction measuring instrument employing this SPR sensor plate. The SPR sensor plate includes: a plate-shaped light waveguide 3 that allows light from a light source 21 to be transmitted therethrough; and a sensing metal film 5 formed on part of a surface of the light waveguide 3. A reflecting metal film 7 is formed on opposite end surfaces of the light waveguide 3 except for a light incident surface 9 and a light exit surface 11 forming inclined surfaces having a same inclination.

13 Claims, 21 Drawing Sheets

SPR SENSOR PLATE AND IMMUNE REACTION MEASURING INSTRUMENT USING THE SAME

BACKGROUND OF THE INVENTION

1. Field of the Invention

The present invention relates to an SPR sensor plate and an immune reaction measuring instrument using the SPR sensor plate, and in particular, to an SPR sensor plate utilizing a surface plasmon resonance (hereafter referred to as "SPR") phenomenon and an immune reaction measuring instrument using this SPR sensor plate.

2. Description of the Related Art

In the field of biochemical analysis, immunoassays have commonly been used to detect a trace amount of protein in subjects. The immunoassay determines the concentration of a predetermined antigen in a subject on the basis of a specific immune reaction between the antigen (protein to be detected) and an antibody (produced using the antigen). With the immunoassay, the antigen to be detected can be measured without the necessity of isolation even if the subject contains plural types of antigens. This is the point where the immunoassay is different from chemical or physical measuring methods.

There are various immunoassays:
① radio immunoassay: RIA method
② enzyme immunoassay: EIA method
③ fluoro immunoassay: FIA method Lately, the RIA method has not often been used due to its need to use isotopes. Additionally, the EIA method is now commonly used due to its ability to easily measure immune reaction. Furthermore, the FIA method is considered to be a sensitive and accurate measuring method. One of various EIA methods which uses a solid phase to measure an antibody is particularly called an "ELISA (enzymelinked immunosorbent assay)", and the ELISA further has the following two methods.

a. indirect method: using an antigen for the solid phase.
b. antibody capturing method: using an anti-Igm antibody for the solid phase.

These ELISA methods are used to determine the amount of an antibody for a particular pathogenic organism and an antibody for an allergen and to screen a monochronal antibody. A measuring kit used for the ELISA method is commonly a microplate having 96 recesses formed therein and on which immune reaction measurements are conducted. Accordingly, a larger number of subjects can be simultaneously measured, and many automated immune reaction measuring instruments have recently been on the market.

Many reagent makers are providing various reagents for the measuring kit for the ELISA method. For example, tPA is an enzyme that indirectly serves to dissolve fibrin present in the blood and which is associated with blood congelation or thrombus. In addition, PAI-1 is an enzyme that restrains the tPA to cause blood congelation or thrombus.

What is called an SPR sensor, used for immune reaction measuring instruments, is well known. The SPR sensor utilizes the surface plasmon resonance phenomenon and carries out measurements on the basis of the following principle: A thin metal film (gold, silver, or the like) of about 50 nm thickness is deposited on a bottom surface of a prism of a large refractive index. Then, predetermined light is allowed to enter the prism side at a critical angle or more toward the thin metal film. Since the thin metal film is translucent at about 50 nm, the light entering the prism side is transmitted through the thin metal film and reaches a surface of the thin metal film opposite to the prism to generate an evanescence field on this surface.

Surface plasmon resonance can be excited on the surface of the thin metal film by adjusting the light incident angle so that the number of waves in the evanescent field equals the number of waves in the surface plasmon resonance. In this case, the number of waves in the surface plasmon resonance depends on the dielectric constant of the thin metal film and on the refractive index of a subject fixed on the surface of the thin metal film opposite to the prism. Thus, the refractive index and dielectric constant of the subject can be determined. In this manner, the optical system and the subject are located opposite to each other across the thin metal film, so that this sensor can be constructed easily.

As an application of the above principle, an SPR sensor for immune reaction measuring instruments employing optical fibers has been developed (manufactured by BIACORE Co., Ltd.; trade name: BIACORE Probe). In this SPR sensor employing optical fibers, a clad is removed from an outer peripheral surface of a tip portion of the optical fiber and an end surface of the tip of the optical fiber is cut flat or polished and then coated with silver. Additionally, the outer peripheral surface of the tip of the optical fiber is coated with a thin metal film (gold or silver or the like). Furthermore, the thin metal film on the outer peripheral surface of the tip of the optical fiber is covered with dielectric film, on which an antibody for use in immune reaction measurements if fixed. Further, the optical fiber has a predetermined light source disposed on the other end side thereof so as to introduce light thereinto.

The immune reaction measuring method for the SPR sensor configured as described above will be described. First, light is introduced into the optical fiber and light of a predetermined wavelength excites the surface plasmon resonance at the tip portion of the optical fiber. The light wavelength exciting the surface plasmon resonance varies with the refractive indices of the dielectric film and the antibody. The intensity of the light of the wavelength that has induced the surface plasmon resonance attenuates. Thus, immune reaction can be measured by comparing the wavelength of the light attenuating most significantly before the immune reaction with that of the light attenuating most significantly after the immune reaction. In addition, an SPR sensor employing a prism in place of optical fibers has been developed.

The above conventional examples have the following disadvantages: If the SPR sensor is formed of an optical fiber, a thin metal film must be formed on an outer peripheral surface of a tip portion of a light waveguide of the optical fiber (for example, Au must be deposited thereon). Since, however, the optical fiber is fine, the thin metal film cannot be appropriately formed.

Additionally, for actual immune reaction measurements, an antibody must be bound to a surface of the thin metal film. Since, however, the tip portion of the light waveguide of the optical fiber is fine and cylindrical, it is disadvantageously difficult to fix the antibody thereto.

In addition, the prism type (using a single wavelength as a light source) carries out immune reaction measurements on the basis of the relationship between the light incident angle and the light intensity, so that it requires a drive section for varying the light incident angle. Consequently, it has a complicated structure.

BRIEF SUMMARY OF THE INVENTION

Object of the Invention

An object of the present invention is to eliminate such disadvantages of the conventional examples to provide an SPR sensor plate which particularly allows the easy fixation of an antibody and the easy retention of a subject and which can be manufactured easily as well as an immune reaction measuring instrument using this SPR sensor plate.

SUMMARY OF THE INVENTION

To attain the above object, the present invention provides an SPR sensor plate comprising an optical waveguide for allowing light from a light source to pass therethrough and a sensing metal film formed on part of a surface of the optical waveguide, wherein the optical waveguide has reflecting metal films formed on opposite end surfaces thereof except for a light incident surface and a light exit surface, and at least one of the incident surface and exit surface is inclined through a predetermined inclination. With this configuration, light is incident on the light waveguide from the incident surface, and the incident light is repeatedly reflected inside the light waveguide. Then, while passing through the light waveguide, the light induces surface plasmon resonance on the sensing metal film. Subsequently, the light is emitted from the exit surface of the light waveguide and is incident on light detecting means. Accordingly, an optical path length producing the surface plasmon resonance is prolonged, and consequently, measuring sensitivity is improved. Additively, since the incident surface or the exit surface is inclined, it becomes easier to set the light source and an optical axis of the light detecting means.

BRIEF DESCRIPTION OF THE DRAWINGS

FIG. 1 shows an SPR sensor plate according to a first embodiment of the present invention.

FIG. 3 is a perspective view showing a variation of the SPR sensor plate according to the first embodiment.

FIG. 4 is a perspective view showing a variation of the SPR sensor plate according to the first embodiment.

FIG. 5 shows an SPR sensor plate according to a second embodiment of the present invention.

FIG. 7 is a perspective view showing a variation of the SPR sensor plate according to the second embodiment.

FIG. 8 is a perspective view showing a variation of the SPR sensor plate according to the second embodiment.

FIG. 13 shows an SPR sensor plate according to a fourth embodiment of the present invention.

FIG. 15 shows an SPR sensor plate according to a fifth embodiment of the present invention.

DETAILED DESCRIPTION OF THE PREFERRED EMBODIMENTS

First Embodiment

A first embodiment of the present invention will be described with reference to the drawings.
[General Outline of the SPR Sensor Plate]

Figure 1A:
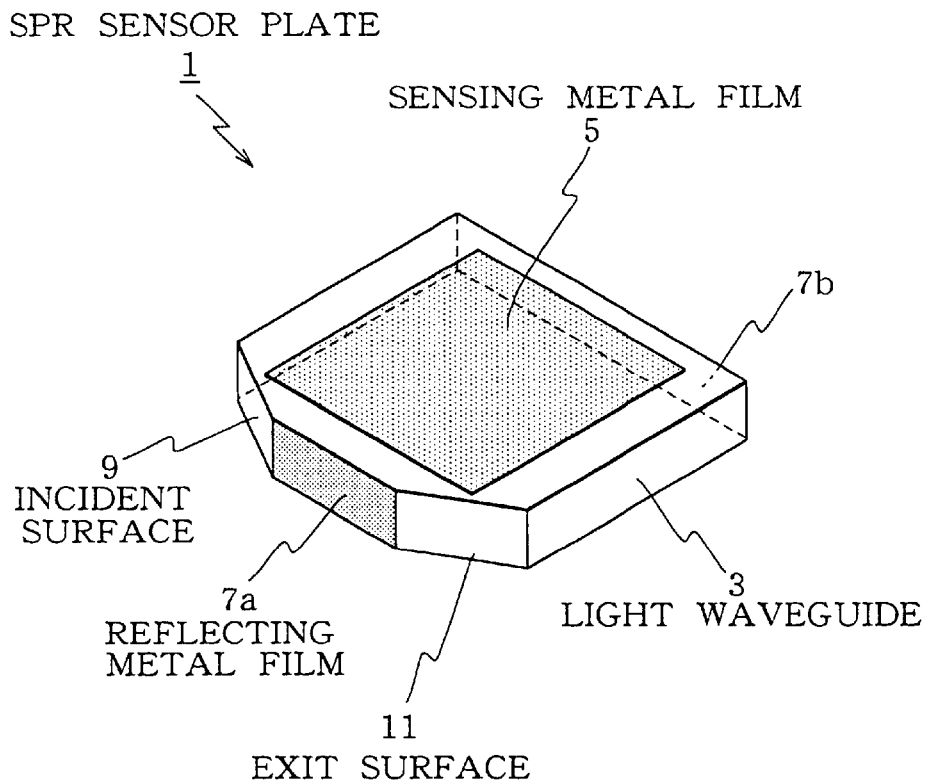
FIG. 1(A) is a general perspective view.
Figure 1B:
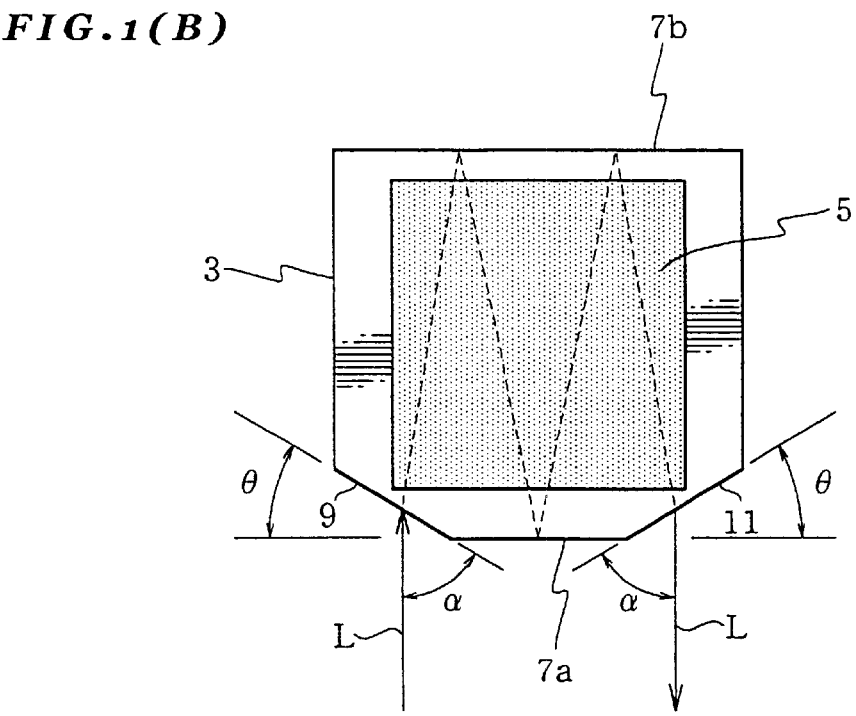
FIG. 1(B) is a top view.

FIG. 1 shows an SPR sensor plate 1 according to this embodiment. In particular, FIG. 1(A) is a general perspective view of the SPR sensor plate 1, and FIG. 1(B) is a top view. The SPR sensor plate 1 of this embodiment comprises a plate-shaped light waveguide 3. More specifically, the SPR sensor plate 1 comprises the light waveguide 3 for allowing light to pass therethrough, a sensing metal film 5 formed on one surface (in this embodiment, the top surface) of the light waveguide 3, and a reflecting metal film 7 formed on a predetermined end surface of the light waveguide 3.
Light Waveguide The light waveguide 3 constituting the SPR sensor plate 1 of this embodiment is composed of glass or plastic. The light waveguide 3 is composed of a transparent material so that light incident on a predetermined incident surface 9 is totally and repeatedly reflected inside the waveguide and emitted from an exit surface 11. The light waveguide 3 is shaped like a plate composed of rectangular plates. In the SPR sensor plate 1 of this embodiment, the light waveguide 3 has the incident surface 9 and the exit surface 11 formed on one end surface thereof. The refractive index of the light waveguide is defined as n1 for convenience.

The planar shape of the light waveguide 3 according to this embodiment is a hexagon obtained by cutting off two surfaces from a rectangle. More specifically, a corner of the rectangular light waveguide 3 comprises a surface inclined through an angle θ. This inclined surface acts as the inclined surface 9 on which light is incident. Additionally, another corner of the light waveguide 3 similarly comprises a surface inclined through the angle θ. This inclined surface acts as the exit surface 11. The incident surface 9 and the exit surface 11 are both formed on the side of a reflecting metal film 7a, described later. The present invention, however, does not require both the incident surface and the exit surface to be inclined. The object of the present invention can be attained by inclining only one of the incident surface and the exit surface. Further, even if both the incident surface and the exit surface are inclined, they need not be inclined through the same angle. This is because the optical axis of a light source, described later, may not be parallel with the optical axis of a light detecting means.

Of the surface of the light waveguide 3, the end surfaces with the incident surface 9 and the exit surface 11 formed thereon and the opposite end surface are polished to be smooth. Additionally, the surface with the above sensing metal surface 5 formed thereon and the opposite surface are polished. This treatment is provided to allow light entering the inside of the light waveguide 3 to be appropriately and repeatedly reflected and then emitted from the exit surface 11. The light incident surface 9 and exit surface 11 are similarly polished and smoothed. This treatment is provided to allow light from a light source (not shown) passing through the light waveguide 3 to be appropriately emitted to the light detecting means (not shown) such as a spectroscope. The incident surface 9 and the exit surface 11 need not necessarily be polished.

On the other hand, those of the end surfaces of the light waveguide 3 on which the incident surface 9 or the exit surface 11 is not formed need not necessarily be polished. This is because light is not often reflected from these surfaces. In contrast, these surfaces may desirably undergo light blocking surface treatment. This treatment is provided to prevent an excess of light other than the light used for immune reaction measurements from entering the light waveguide 3. Specifically, these surfaces may be formed like a frosted glass, coated with aluminum, or painted black. The present invention, however, is not limited to such processing but these surfaces may be processed in any manner as long as they can be adapted to restrain the incidence of light.

Sensing Metal Film

Of the surface of the light waveguide 3, a large surface (in this embodiment, the top surface in this figure) has the sensing metal film 5 formed thereon. The sensing metal film 5 is formed to be planar except for the peripheral portion of the top surface of the light waveguide 3. The sensing metal film 5 is used to induce the surface plasmon resonance phenomenon and has an antigen and an antibody bound thereto during actual immune reaction measuring. In this embodiment, the sensing metal film 5 is formed on the top surface of the light waveguide 3 except for its peripheral portion, but the present invention is not limited to this. That is, the sensing metal film 5 may be formed all over the top surface of the light waveguide 3. Additionally, the shape of the sensing metal film 5 is not limited to the rectangle as shown in the figure. That is, it may be a trapezoid or a triangle as long as the sensing metal film 5 is formed at a location where measuring light is reflected.

Various metals may be used for the sensing metal film 5, but specifically gold (Au), silver (Ag), nickel (Ni), or the like is desirable. Further, various methods may be used to form the sensing metal film 5, but for example, the vacuum evaporation process or the sputtering method is desirable. Additionally, the durability of the sensing metal film (its compatibility with and adhesion to glass) is improved by forming it on glass or plastic via a Cr film or the like. The Cr film or the like generally has a thickness of several nm. This is because the above processes enable the formation of a metal film of a uniform thickness.

For actual immune reaction measurements, on the surface of the light waveguide 3, a dielectric film (not shown) is formed on the sensing metal film 5, and an antibody (or antigen) is bound to a surface of the dielectric film. An appropriate antibody (or antigen) is selected depending on the antigen (or antibody) contained in the subject to be measured. This is because when the antibody that specifically reacts to the antigen contained in the subject is bound to the antigen, the presence of this particular antigen in the subject can be determined by means of immune reaction measurements.

Reflecting Metal Films

Next, the reflecting metal films 7a and 7b will be described. The reflecting metal films 7a and 7b reflect light introduced into the light waveguide 3. More specifically, the reflecting metal films 7a and 7b are formed on those of the end surfaces of the light waveguide on which the incident surface 9 and the exit surface 11 are formed, and on the opposite surface. Since, however, the incident surface 9 and the exit surface 11 must transmit light through themselves, the reflecting metal film 7a is not formed on these portions. Accordingly, the reflecting metal film 7a is formed on the above end surfaces except for the portions of the incident surface 9 and the exit surface 11. On the other hand, the surface on which the incident surface 9 or the exit surface 11 is not formed is entirely formed into the reflecting metal film 7b. The present invention, however, is not limited to this. That is, the reflecting metal films 7a and 7b may be formed only in those portions which are principally irradiated with light.

The reflecting metal films 7a and 7b are formed of gold (Au), silver (Ag), aluminum (Al), or the like. The reflecting metal films 7a and 7b are formed by means of the vacuum evaporation process or the sputtering process. The present invention, however, is not limited to these processes as long as uniform reflecting surfaces can be formed. In this case, if the reflecting metal films 7a and 7b are formed of metal such as Ag which is likely to be oxidized, metal films such as $SiO_2$ or Au which are unlikely to be oxidized are desirably coated on the reflecting metal films 7a and 7b to protect them.

[Incident Surface and Emitting Surface]

Next, the incident surface 9 and the exit surface 11 will be described. In the SPR sensor plate 1 according to this embodiment, the incident surface 9 and the exit surface 11 are formed on the same end surface side. Specifically, the incident surface 9 and the exit surface 11 are formed on the corresponding ends on one end surface of the light waveguide 3. As shown in FIG. 1(B), measuring light is incident on the incident surface 9 and is repeatedly reflected inside the light waveguide 3 and then emitted from the exit surface 11. In this embodiment, the dimensions of each section are set so that light is emitted from the exit surface 11 after being reflected inside the light waveguide 3 three times.

Figure 2:
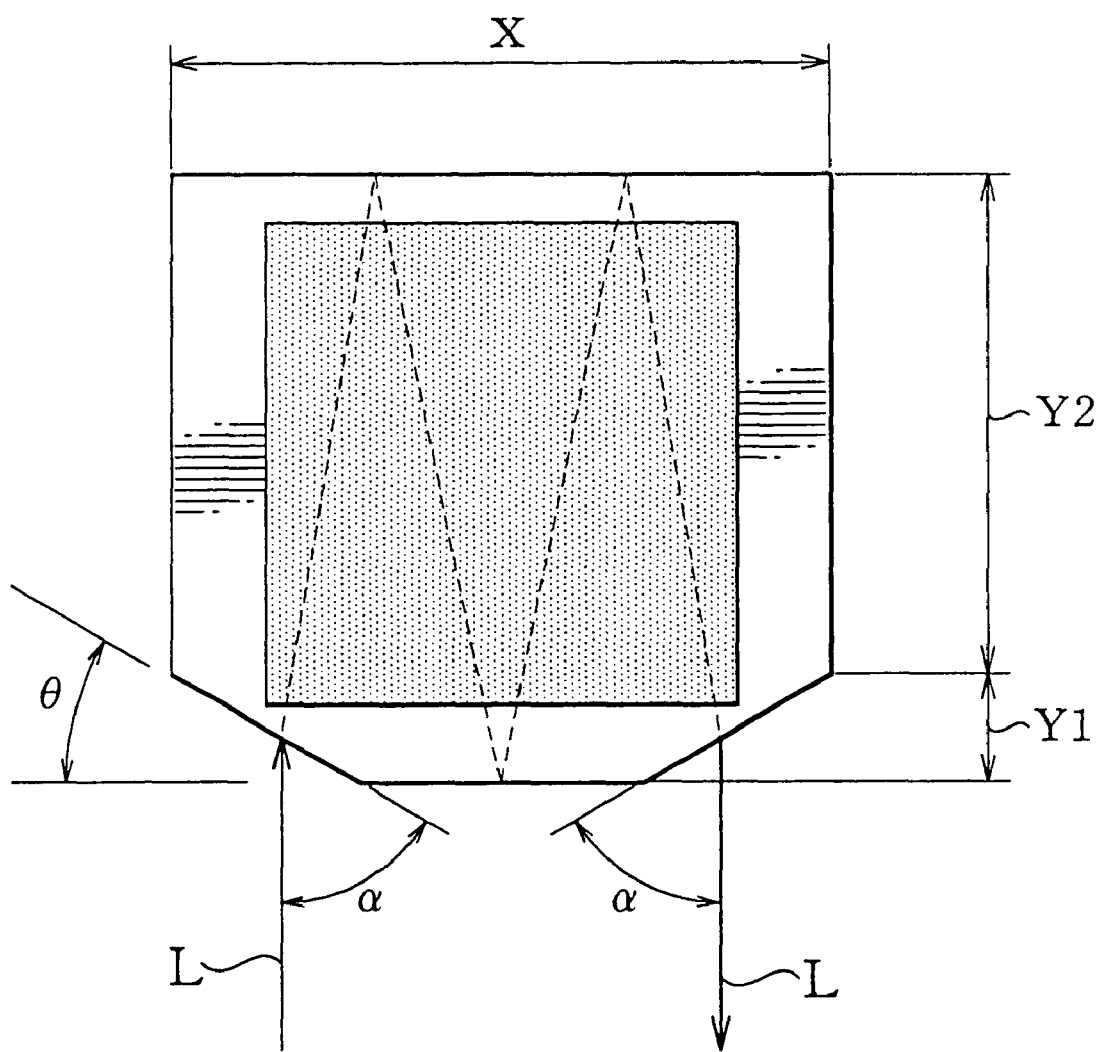
FIG. 2 is a top view useful in explaining dimensions of the SPR sensor plate disclosed in FIG. 1.

Specific dimensions of this SPR sensor plate will be shown below by way of example. As shown in FIG. 2, the width-wise height of the light waveguide 3 is defined as X, the height of the inclined surfaces of the incident surface 9 and the exit surface 11 is defined as Y1, and the height from the inclined surfaces is defined as Y2. The incidence angle of light from the incident surface 9 is defined as α. In addition, air has a refractive index of 1. Furthermore, the number of times that light is reflected inside the light waveguide 3 is defined by $2a-1$ (a denotes a positive real number). Further, light is allowed to enter a central portion of the incident surface 9. Then, the dimensions of the light waveguide 3 are set so as to establish the following equation:

$$X=Y1/(\tan\theta)+\{(2a-1)Y1+(2a)Y2\}\times\tan[\{(\pi/2)-\theta\}-\arcsin\{(1/(n1))\times\cos\alpha\}]$$

where $$\theta=\pi/2-\alpha \text{ and } a=2.$$

With the SPR sensor plate 1 configured as described above, as shown in FIG. 1(B), light L incident on the incident surface 9 is refracted through a boundary surface of the light waveguide 3 while passing through the light waveguide 3, and is reflected by the opposite reflecting metal film 7b. The reflected light is reflected again by the reflecting metal film 7a on the incident surface 9 side and further by the opposite reflecting metal film 7b, and is finally emitted from the exit surface 11 of the light waveguide 3. At this time, since the light waveguide 3 has a homogeneous structure and the reflecting metal films 7a and 7b are parallel with each other, if the light incidence angle is $\alpha$, then the emitting angle is also $\alpha$. On the other hand, the light is totally reflected in the thickness direction of the light waveguide 3. Consequently, most of the light is transmitted through the light waveguide 3. As a result, this SPR sensor plate has a significantly longer optical path than in the case where light is linearly transmitted through the light waveguide 3. Thus, the distance that the surface plasmon resonance occurs increases to improve the sensitivity for immune reaction measurements.

[Immune Reaction Measurements]

Next, immune reaction measurements using the above SPR sensor plate 1 will be described. The SPR sensor plate 1 shown in FIG. 1(B), the bottom surface of the light waveguide 3 is exposed to air. In this case, the refractive index n1 of the light waveguide 3 must be larger than that of air (=1.0) in order to totally reflect light inside the light waveguide 3 though the bottom surface of the light waveguide 3 is composed of air. Accordingly, the SPR sensor plate 1 of this embodiment comprises a light waveguide meeting such conditions.

For actual immune reaction measurements, before a subject is attached to the sensing metal film 5 of the SPR sensor plate 1, light is allowed to enter the light waveguide 3 and the distribution of wavelengths obtained is determined. Then, a subject containing a predetermined antigen (or antibody) is stored on the portion of the sensing metal film 5. Accordingly, if the subject contains an antigen that specifically reacts to the antibody bound to the dielectric film, immune reaction occurs. After the immune reaction has occurred, light is allowed to enter the light waveguide 3 to induce the surface plasmon resonance on the sensing metal film 5. Thus, the intensity of light of a particular wavelength that induces the surface plasmon resonance attenuates.

[Variations]

Next, variations of this embodiment will be described.

[Variation 1-1]

Figure 3A:
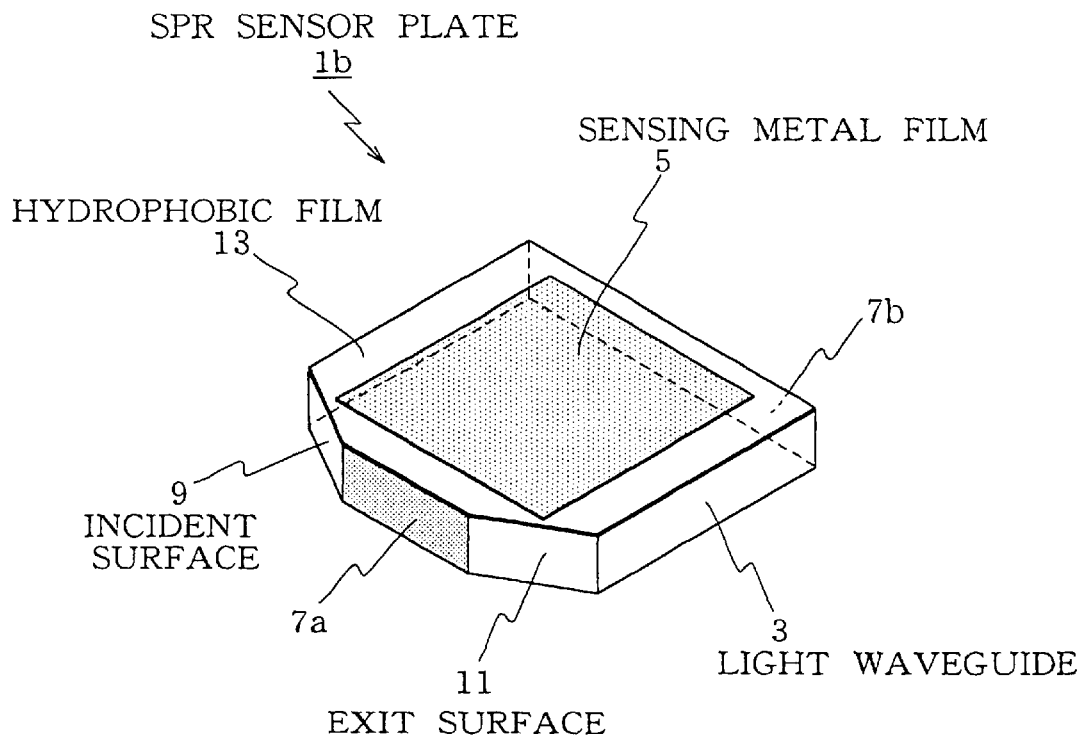
FIG. 3(A) shows a variation 1-1.

FIG. 3(A) is a perspective view showing an SPR sensor plate 1b according to a variation 1-1 of this embodiment. This variation has the same basic configuration as the above SPR sensor plate 1 has. This variation, however, is different therefrom in that the surface on the sensing metal film 5 side is covered with a hydrophobic film 13. That is, the light waveguide 3 itself is the same as that used in the above SPR sensor plate 1. The hydrophobic film 13 is coated on the peripheral portion of the top surface of the light waveguide 3 except for the sensing metal film 5. The hydrophobic film 13 is made of a fluorine-based resin, which repels water; thus, when the subject is injected in the portion of the sensing metal film 5, it remains therein due to the surface tension of the subject itself.

If the hydrophobic film 13 has a refractive index n2, the relationship with the refractive index n1 of the light waveguide 3 is n1>n2 (total-reflection condition). Since such a refractive index condition is met, light is totally reflected inside the light waveguide 3 to enable correct immune reaction measurements. Various resins, for example, PTFE (Poly Tetra Fluoro Ethylene), FEP (Fluorinated Ethylene Propylene copolymer), PFA (tetra fluoro ethylene-PerFluoro Alkylvinyl ether coploymer), and ETFE (Ethylene Tetra Fluoro Ethylene) may be used for the hydrophobic film 13. Various processes may be used to form the hydrophobic film 13, but the spin coat process, the dip coat process, or the roll coat process is desirably used. Alternatively, the hydrophobic film 13 may be formed using the vacuum evaporation process or the like.

[Variation 1-2]

Figure 3B:
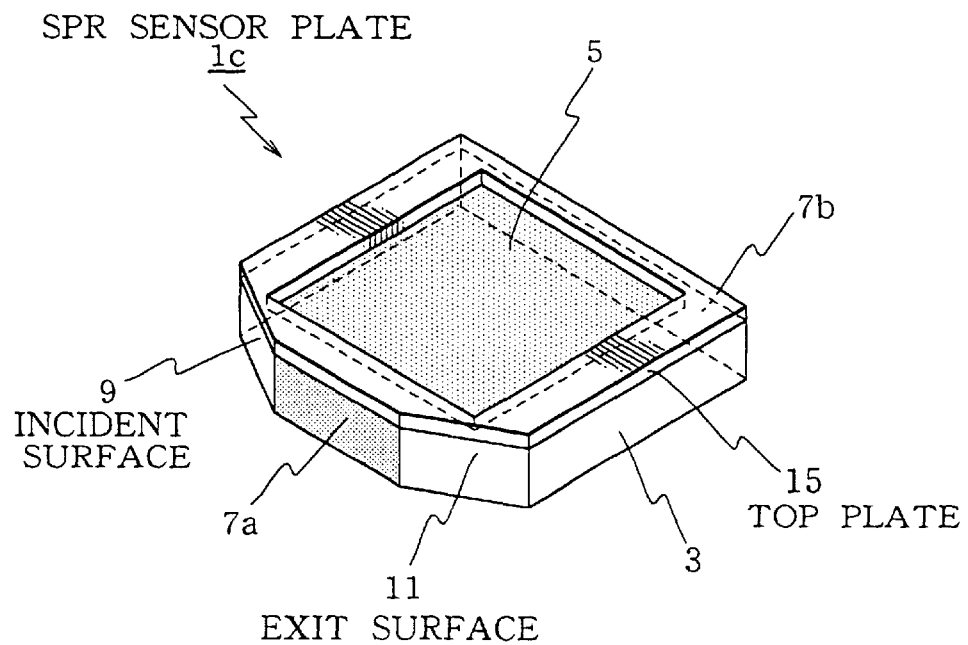
FIG. 3(B) shows a variation 1-2.

Next, an SPR sensor plate 1c according to a variation 1-2 of this embodiment will be described with reference to FIG. 3(B). This variation is characterized in that a top plate 15 is installed on the top surface (on which the sensing metal film 5 is formed) of the light waveguide 3. The top plate 15 is composed of glass, plastic, or the like so that if its refractive index is defined as n3, the condition n1>n3 (total-reflection condition) is met. Thus, light traveling through the light waveguide 3 is totally reflected by the boundary surface between the light waveguide 3 and the top plate 15 to return to the interior of the light waveguide 3.

Various methods may be used to join the light waveguide 3 and the top plate 15 together. For example, they may be jointed together by means of an adhesive or may be welded together by heating the boundary surface. They may also be stuck together by applying fat and oil to the boundary surface. In this case, the adhesive or the like inserted between the waveguide 3 and the top plate 15 must have a smaller refractive index than that n1 of the light waveguide 3.

The top plate 15 must be shaped to cover the top surface of the light waveguide 3 except for the portion of the sensing metal film 5. That is, the peripheral portion of the top surface of the light waveguide 3 is covered with the top plate 15. Accordingly, the portion of the sensing metal film 5 is recessed relative to its peripheries by a distance equal to the thickness of the top plate 15; the subject is stored in this recess. Thus, even if a larger amount of subject is injected into the recess, the subject is prevented from leaking from the SPR sensor plate 1c. Although the top plate 15 according to this variation has the rectangular through-hole in its central area, the shape of the through-hole is not particularly limited. That is, various shapes may be used so as to correspond to the shape of the sensing metal film.

[Variation 1-3]

Figure 4A:
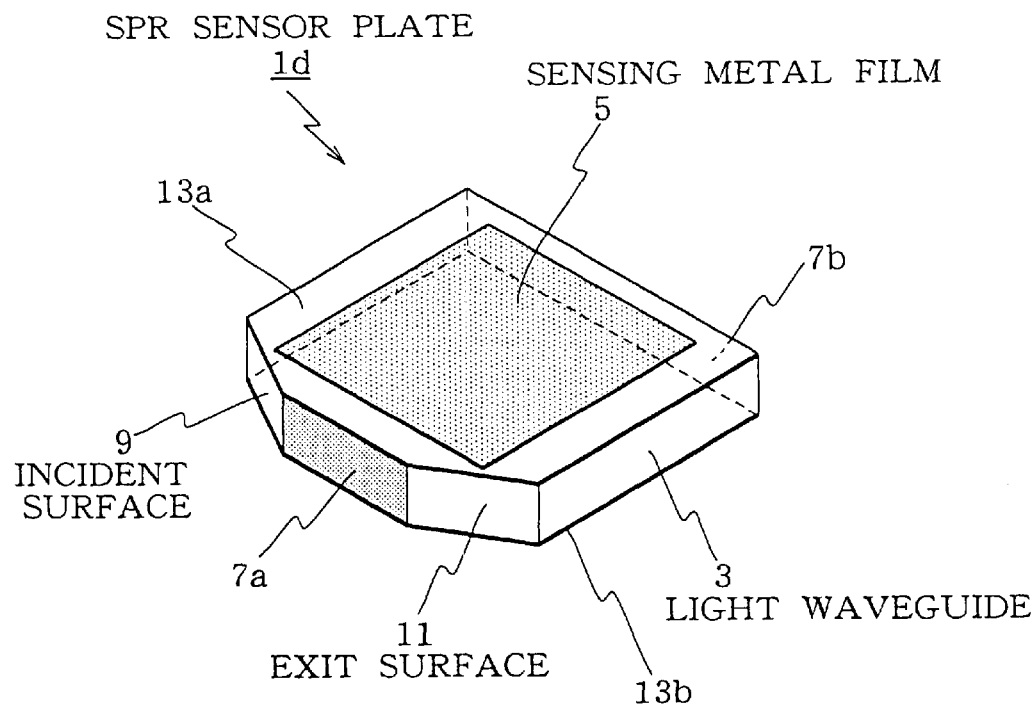
FIG. 4(A) shows a variation 1-3.

Next, a variation 1-3 of this embodiment will be described with reference to FIG. 4(A). An SPR sensor plate 1d according to this variation is characterized in that both the top surface (on which the sensing metal film 5 is formed) and bottom surface of the light waveguide 3 are coated with hydrophobic films 13a and 13b. The SPR sensor plate 1d is otherwise the same as the variation shown in FIG. 3(A). However, the bottom surface of the light waveguide 3 is entirely coated with the hydrophobic film 13b. This is because the sensing metal film 5 is not formed on the bottom surface of the light waveguide 3. The material of the hydrophobic film 13 is similar to that shown in FIG. 3(A), and for example, PTFE, FEP, PFA, or ETFE may be used.

When the hydrophobic film coated on the bottom surface of the light waveguide 3 has a refractive index n4, the refractive indices of the relevant members must be n1>n2 and n1>n4, or n1>n2=n4. These conditions are required to cause total reflection inside the light waveguide 3.

[Variation 1-4]

Figure 4B:
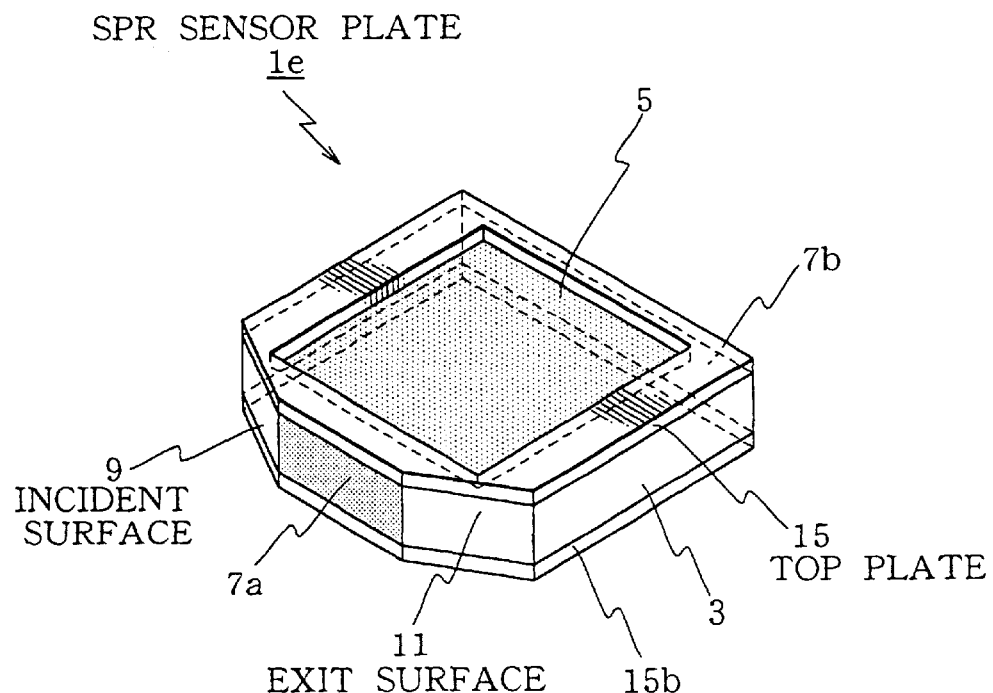
FIG. 4(B) shows a variation 1-4.

Next, a variation 1-4 of this embodiment will be described with reference to FIG. 4 (B). An SPR sensor plate 1e according to this variation has the same main components as the variation shown in FIG. 3(B) has. This variation, however, differs from the variation in FIG. 3(B) in that in addition to the top surface of the light waveguide 3, its bottom surface has a bottom plate 15b installed thereon and composed of a material similar to that of the top plate 15. That is, the bottom plate 15b composed of glass or plastic is installed all over the bottom surface of the light waveguide 3.

When the bottom plate 15b installed on the bottom surface of the light waveguide 3 has a refractive index n5, the refractive indices of the relevant members must be n1>n3 and n1>n5, or n1>n3=n5.

Second Embodiment

Next, a second embodiment of the present invention will be described with reference to FIGS. 5 to 8. This embodiment has the same basic components as the above first embodiment has. An SPR sensor plate if according to this embodiment, however, is characterized in that the incident surface 9 and the exit surface 11 are formed on the opposite end surfaces.

Figure 5A:
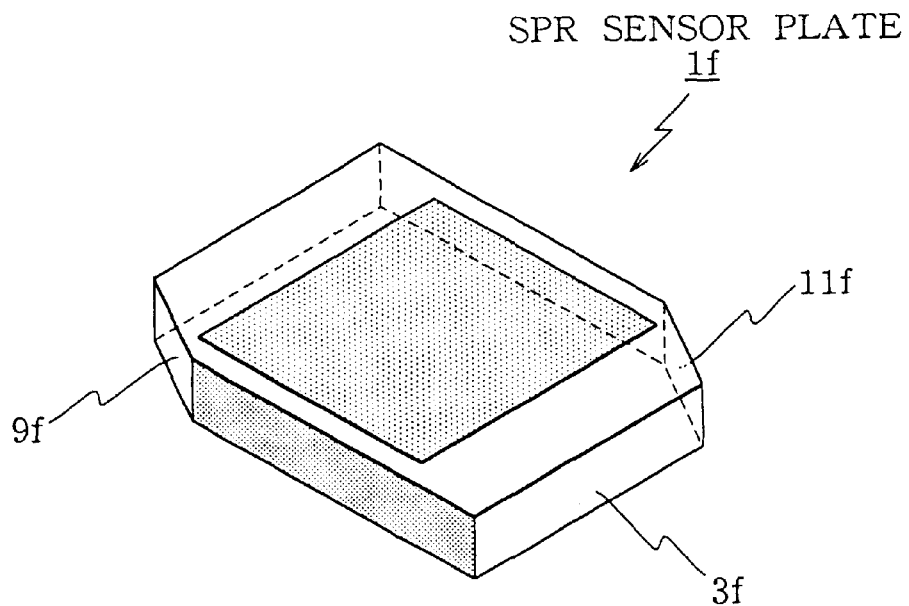
FIG. 5(A) is a general perspective view.
Figure 5B:
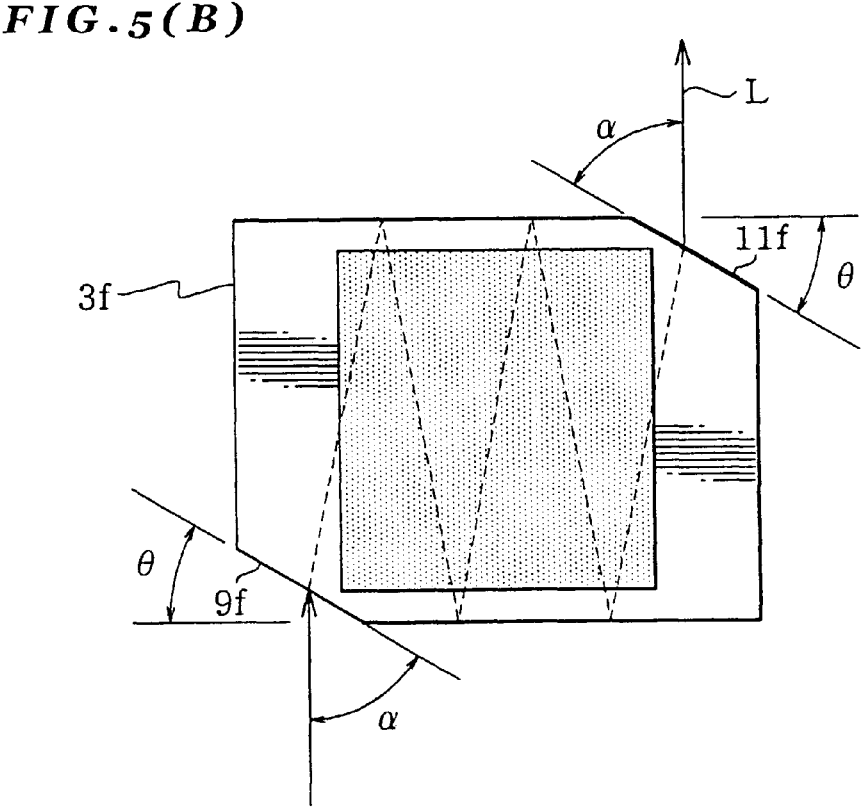
FIG. 5(B) is a top view.
Figure 6:
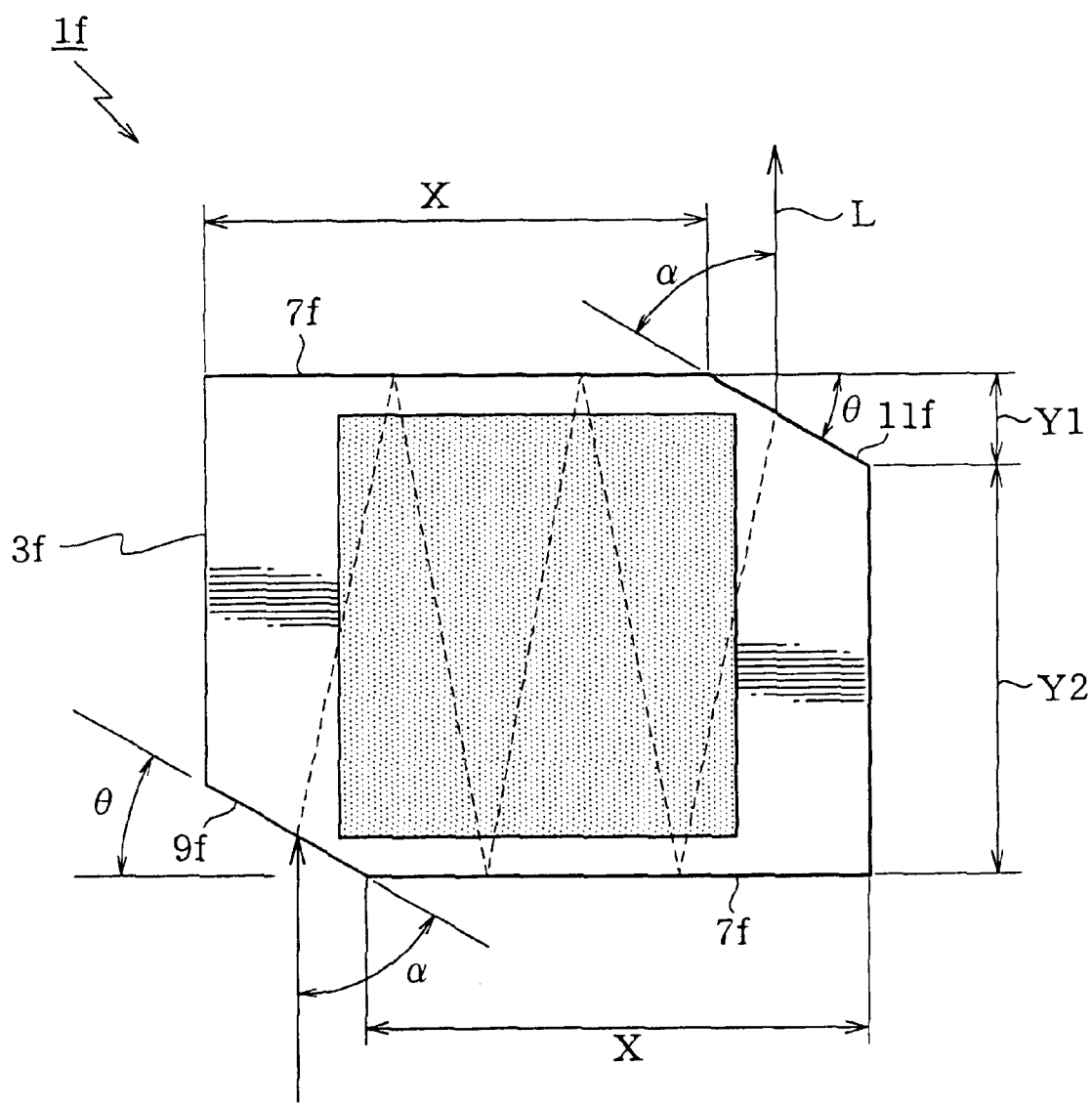
FIG. 6 is a top view useful in explaining dimensions of the SPR sensor plate disclosed in FIG. 5.

Specifically, in the SPR sensor plate 1f shown in FIG. 5, a light incident surface 9f is located closer to the reader (in FIG. 5(B), in its lower part), while an exit surface 11f is located further from the reader (in FIG. 5(B), in its upper part). Specific dimensions of this SPR sensor plate will be shown below by way of example. That is, as shown in FIG. 6, in the width direction of this SPR sensor plate 3f, the length from an end of the light waveguide 3f to a location thereof where the inclined surface (incident surface 9f or exit surface 11f) starts is defined as X. In the height direction, the height of the inclined surface is defined as Y1, and the length from an end of the inclined surface to the lower-most portion is defined as Y2. The incident angle of light is defined as α. In addition, air has a refractive index of 1. Furthermore, light is assumed to be reflected inside the light waveguide 3f 2a times (a denotes a positive real number). Then, the dimensions of the light waveguide 3f are set so as to establish the following equation:

$$X=\{(2a)Y1+(2a+1)Y2\} \times \tan[\{(\pi/2)-\theta\}-\arc\sin\{(1/(n1)) \times \cos \alpha\}]$$

where $\theta=\pi/2-\alpha$ and $a=2$.

Light entering the light waveguide 3 from the incident surface 9f is repeatedly reflected inside the light waveguide 3f and then emitted from the exit surface 11f on the opposite end surface. In the meantime, light is reflected four times by the boundary surface between the light waveguide 3f and the reflecting metal film 7f. The light is emitted from the exit surface 11f at the angle α, which is also measured on incidence.

When the incident surface 9 is thus formed on one side of the light waveguide 3, whereas the exit surface 11 is formed on the other side, the light source and accessories such as a spectroscope can be arranged on different sides.

[Variations]

Next, variations of the second embodiment will be described.

[Variation 2-1]

Figure 7A:
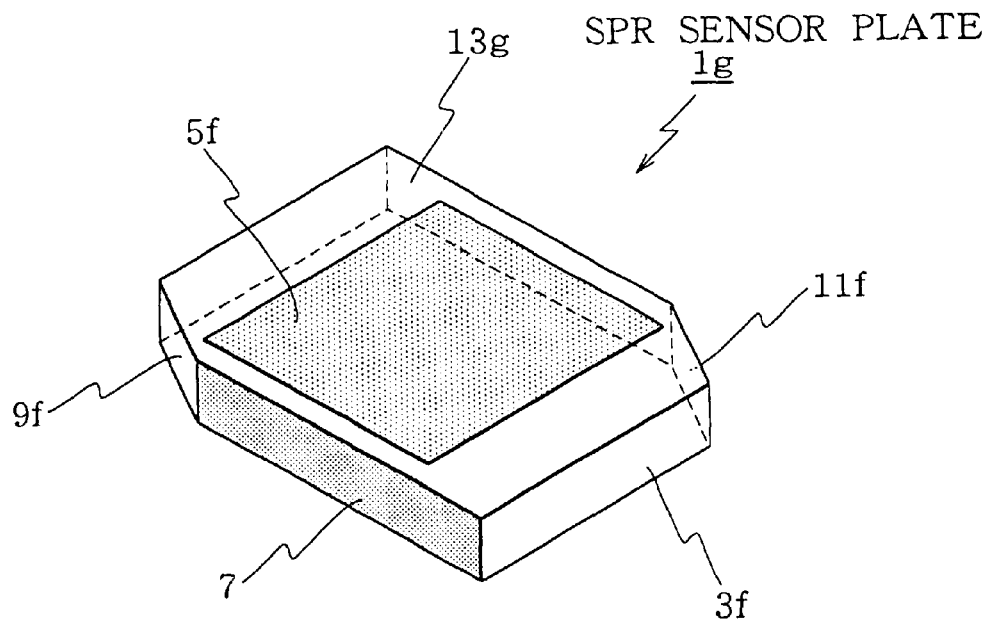
FIG. 7(A) shows a variation 2-1.

FIG. 7(A) is a perspective view showing an SPR sensor plate 1g according to a variation 2-1 of this embodiment. This variation has the same basic configuration as the above SPR sensor plate if has. This variation, however, is different therefrom in that the surface on the sensing metal film 5 side is covered with a hydrophobic film 13g. That is, the light waveguide 3f itself is the same as that used in the above SPR sensor plate 1f. The hydrophobic film 13g is coated on the peripheral portion of the top surface of the light waveguide 3f except for the sensing metal film 5f. The hydrophobic film 13g is made of a fluorine-based resin, which repels water; thus, when the subject is injected in the portion of the sensing metal film 5f, it remains therein due to the surface tension of the subject itself.

The refractive indices and material of the hydrophobic film 13g and its formation method are similar to those described in the first embodiment.

[Variation 2-2]

Figure 7B:
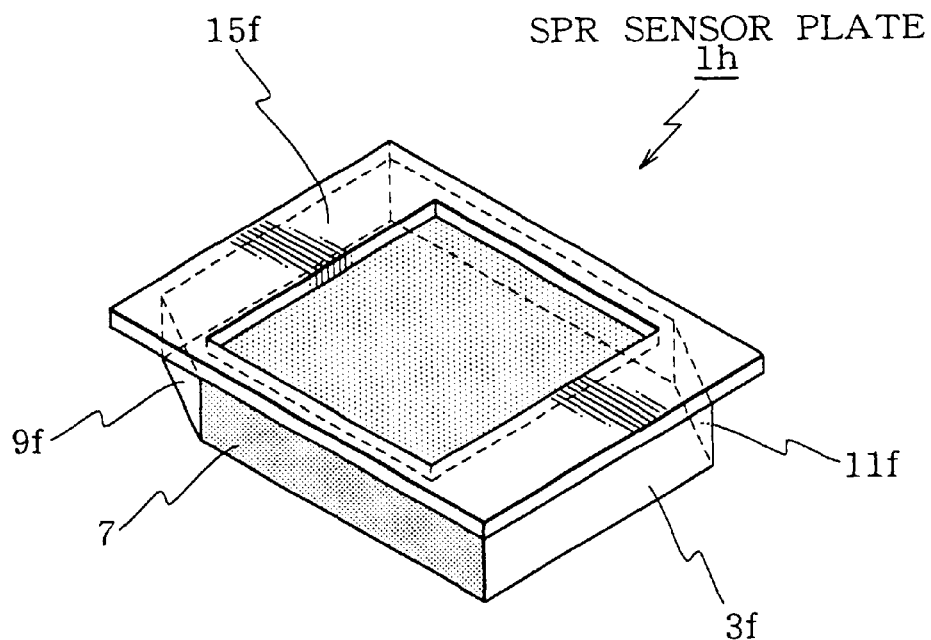
FIG. 7(B) shows a variation 2-2.

Next, an SPR sensor plate 1h according to a variation 2-2 of this embodiment will be described with reference to FIG. 7(B). This variation is characterized in that a top plate 15f is installed on the top surface (on which a sensing metal film 5f is formed) of the light waveguide 3f. The top plate 15f is composed of glass, plastic, or the like. The refractive index of the top plate 15, the method for joining the top plate 15 to the light waveguide 3f, the shape of the top plate 15f, and the like are similar to those described in the first embodiment.

[Variation 2-3]

Figure 8A:
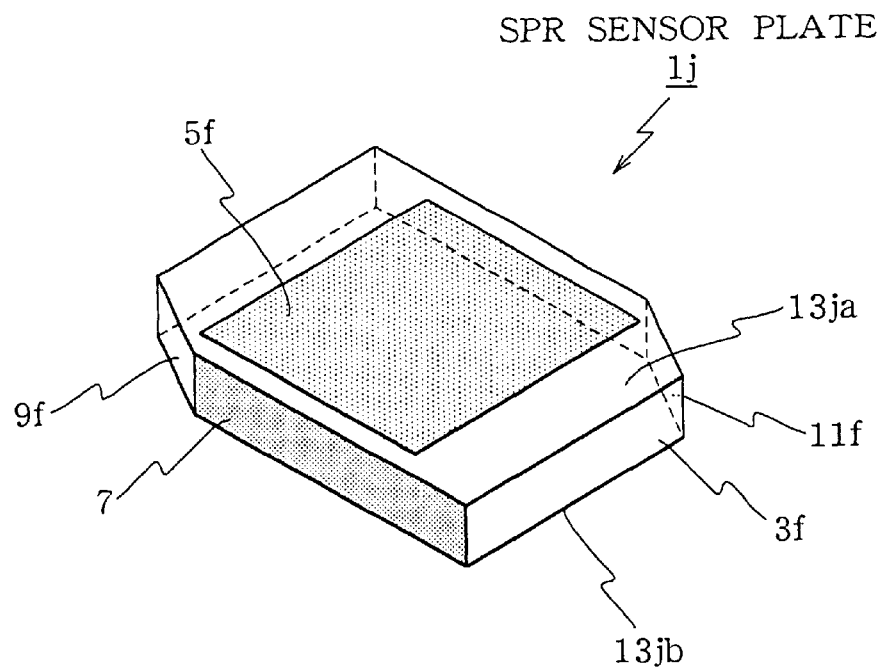
FIG. 8(A) shows a variation 2-3.

Next, a variation 2-3 of this embodiment will be described with reference to FIG. 8(A). An SPR sensor plate 1j according to this variation is characterized in that both the top surface (on which the sensing metal film 5f is formed) and bottom surface of the light waveguide 3f are coated with hydrophobic films 13ja and 13jb. The other points are the same as those of the variation shown in FIG. 7(A). However, the bottom surface of the light waveguide 3f is entirely coated with the hydrophobic film 13jb. This is because the sensing metal film 5f is not formed on the bottom surface of the light waveguide 3f. The material of the hydrophobic films 13ja and 13jb is similar to that shown in FIG. 3(A), and for example, PTFE, FEP, PFA, or ETFE may be used.

[Variation 2-4]

Figure 8B:
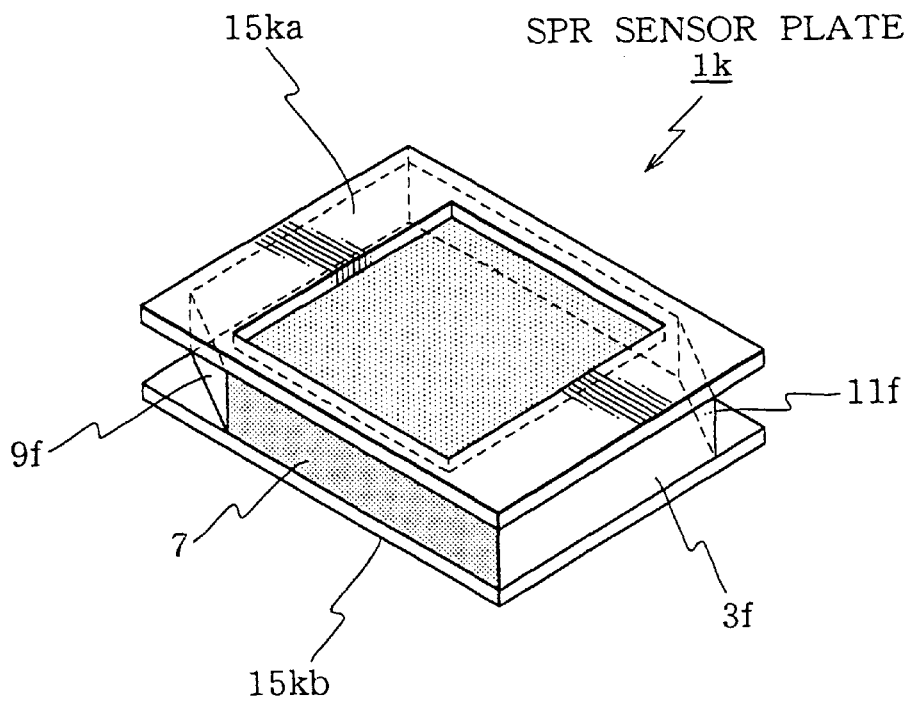
FIG. 8(B) shows a variation 2-4.
Figure 9:
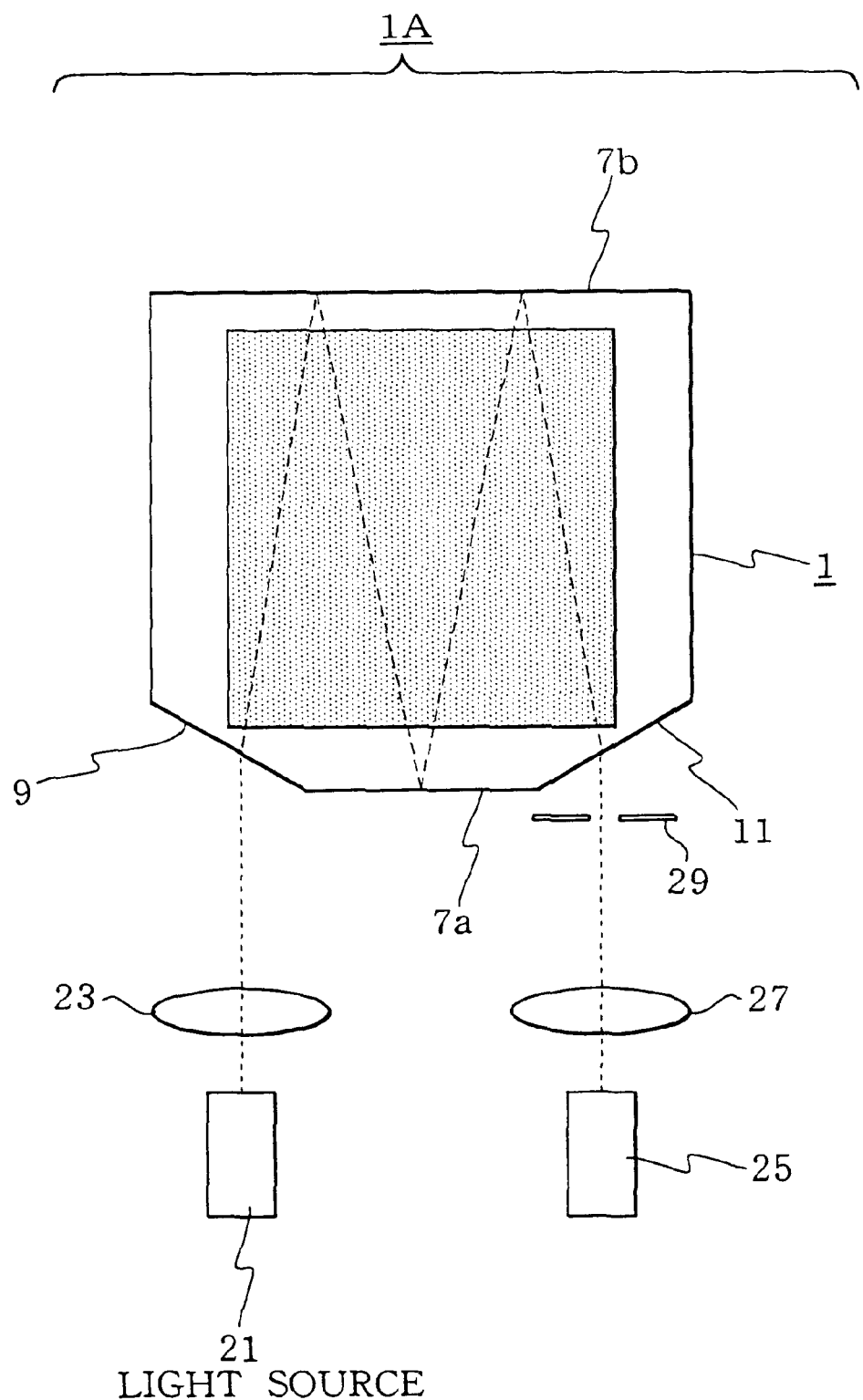
FIG. 9 is a view showing an immune reaction measuring instrument according to a third embodiment of the present invention.

Next, a variation 2-4 of this embodiment will be described with reference to FIG. 8(B). An SPR sensor plate 1k according to this variation has the same main components as the variation shown in FIG. 7(B) has. This variation, however, differs from the variation in FIG. 7(B) in that a bottom plate 15kb is installed on the bottom surface of the light waveguide 3f. That is, the bottom plate 15kb composed of glass or plastic is installed all over the bottom surface of the light waveguide 3f.

When the bottom plate 15kb installed on the bottom surface of the light waveguide 3f has the refractive index n5, the refractive indices of the relevant members must be n1>n3 and n1>n5, or n1>n3=n5. This is the same as in each of the above described embodiments.

Third Embodiment

Next, a third embodiment of the present invention will be described with reference to FIGS. 9 to 12. This embodiment is an example of an immune reaction measuring instrument using the above SPR sensor plate. An immune reaction measuring instrument 1A, shown in FIG. 9, uses the SPR sensor plate 1 described in the first embodiment. The immune reaction measuring instrument 1A comprises a light source 21 for applying predetermined light, a first condenser lens 23 for condensing the light from the light source 21, a second condenser lens 27 for condensing the light emitted from the exit surface 11, a light detecting means 25 for receiving the light condensed by the second condenser lens 27, and a slit 29 arranged between the SPR sensor plate 1 and the second condenser lens 27.

The light source 21 applies light L of a predetermined wavelength band; specifically, it comprises a white LED lamp. In this embodiment, the distribution of the wavelength of light passing through the SPR sensor plate 1 is analyzed before and after immune reaction to thereby measure the immune reaction. Accordingly, the light source 21 desirably supplies light having a stable wavelength distribution. Commercially available white LED lamps apply light of a wavelength band between about 450 and 750 nm. The light source 21 may be different from the above white LED lamp as long as it can apply light of a certain wavelength band. Specifically, the light source 10 may be a halogen lamp.

The white LED lamp generally has a directionality (irradiation angle) corresponding to an angle between 20° and 60°. In contrast, halogen lamps have an irradiation angle of 180° or more. Thus, with a very directional light source such as a white LED, light may be allowed to enter the SPR sensor plate 1 without using any special condenser lens.

If the light source 21 comprises a white LED lamp, its costs are one-tenth of those of a halogen lamp, and its power consumption is about one-thirtieth of that of a halogen lamp. Thus, this device can be driven by batteries, so that its size can be reduced and it can be transported easily.

Next, the light detecting means 25 will be described. The light detecting means used to measure the distribution of wavelengths comprises a spectroscope. Alternatively, it may be a photodiode. In this case, a wavelength that may attenuate on immune reaction is predicted in advance, and a filter through which only light of this wavelength can be transmitted is provided so that the immune reaction can be measured by determining that the light of this wavelength has attenuated. Alternatively, a plurality of photodiodes may be provided and each provided with filters that allows light of different wavelengths to pass therethrough so that the immune reaction can be measured by analyzing the attenuation of the light of each wavelength. Additionally, the condenser lenses 23 and 27 may comprise spherical lenses, non-spherical lenses, one-side convex lenses, or other lenses.

When the incident surface 9 and the exit surface 11 are thus inclined, the optical axes of the light source 21 and the light detecting means 25 may be parallel with each other. Thus, the optical system can be designed more easily, and the measuring accuracy can be improved. An appropriate inclination θ is selected for the inclined surfaces taking the difference in the refractive index between air and the light waveguide into consideration.

Figure 10:
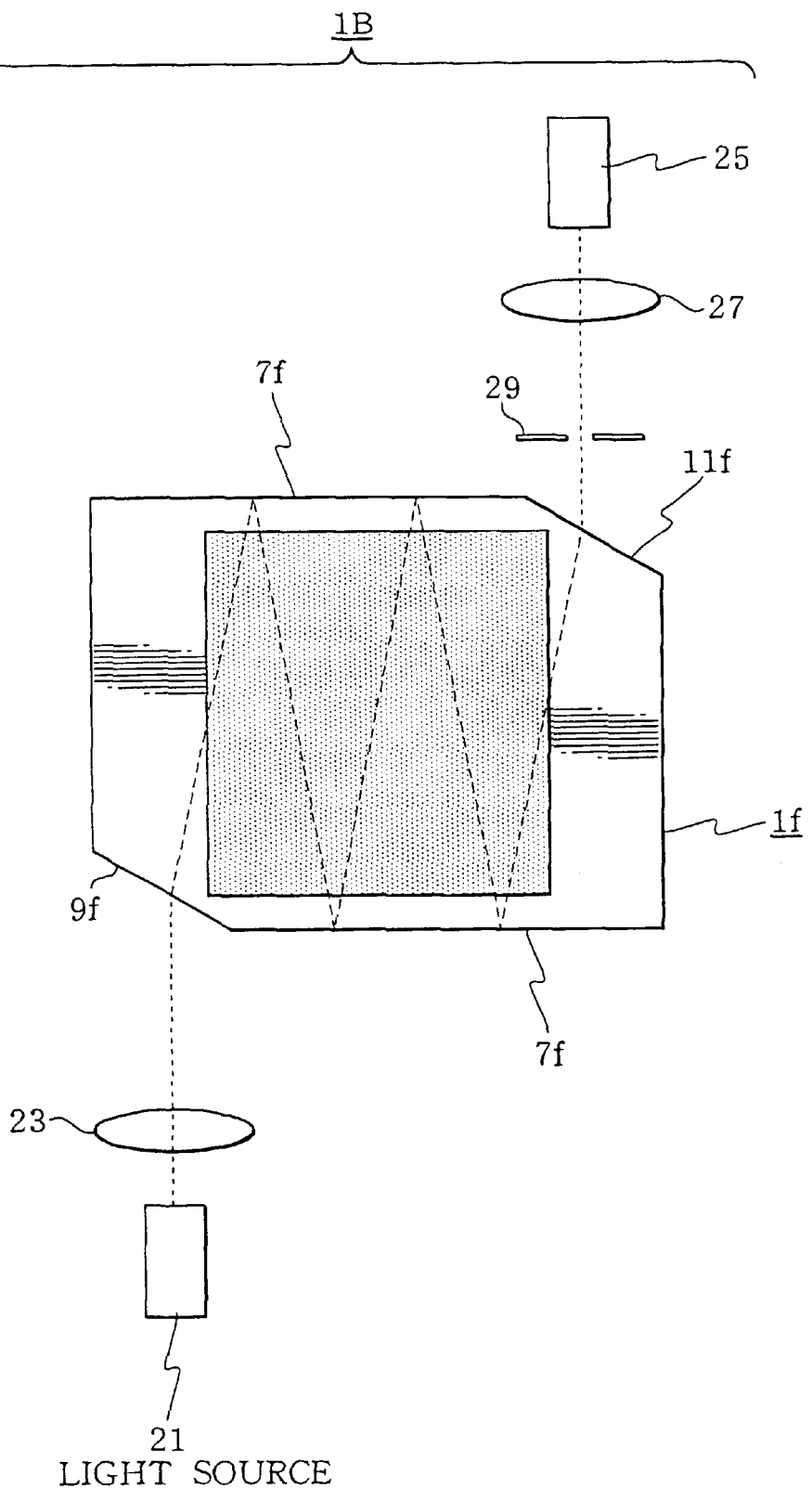
FIG. 10 is a view showing another example of the immune reaction measuring instrument according to the third embodiment of the present invention.

FIG. 10 shows an immune reaction measuring instrument 1B using the SPR sensor plate if according to the second embodiment. This is substantially the same as the above immune reaction measuring device 1A except that the incident surface 9f and the exit surface 11f are on opposite end surfaces. The light source 21 and the light detecting means 25 are disposed on opposite sides correspondingly to the incident surface 9f and the exit surface 11f.

Figure 11:
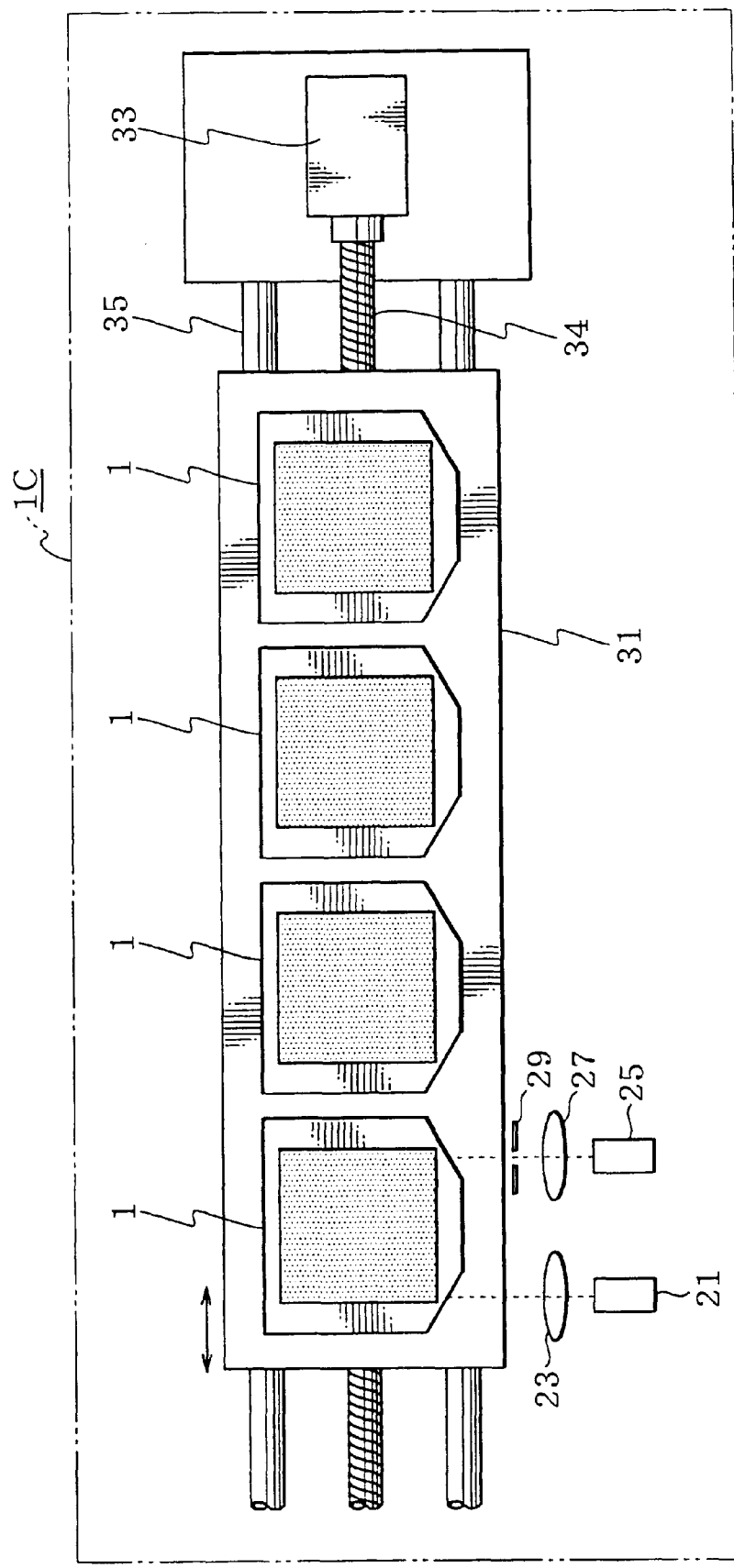
FIG. 11 is a view showing yet another example of the immune reaction measuring instrument according to the third embodiment of the present invention.

FIG. 11 is a top view showing an immune reaction measuring instrument 1C in which a plurality of SPR sensor plates 1 can be installed. The immune reaction measuring instrument 1C carries the SPR sensor plates 1 on a stage 31 that is movable. The stage 31 is moved by means of a screw 34 and a monitor 33 rotating the screw 34.

More specifically, the stage 31 is slidably fixed to two guide shafts 35 so as to movable along them. The stage 31 has an external thread formed in the bottom surface thereof and on which the screw 34 is fitted. Thus, as the motor 33 is rotated, the screw 34 rotates. As the screw 34 rotates, the stage 31 moves along the guide shafts 35. In this case, if the motor 33 is a stepping motor, the stage 31 can be positioned accurately.

On the other hand, neither the light source 21 nor the light detecting means 25 nor the condenser lenses 23 nor 27 moves. That is, the movement of the stage 31 allows the switching of the SPR sensor plates 1 for immune reaction measurements. Thus, neither the light source 21 nor the light detecting means 25 requires any complicated movement means.

Figure 12:
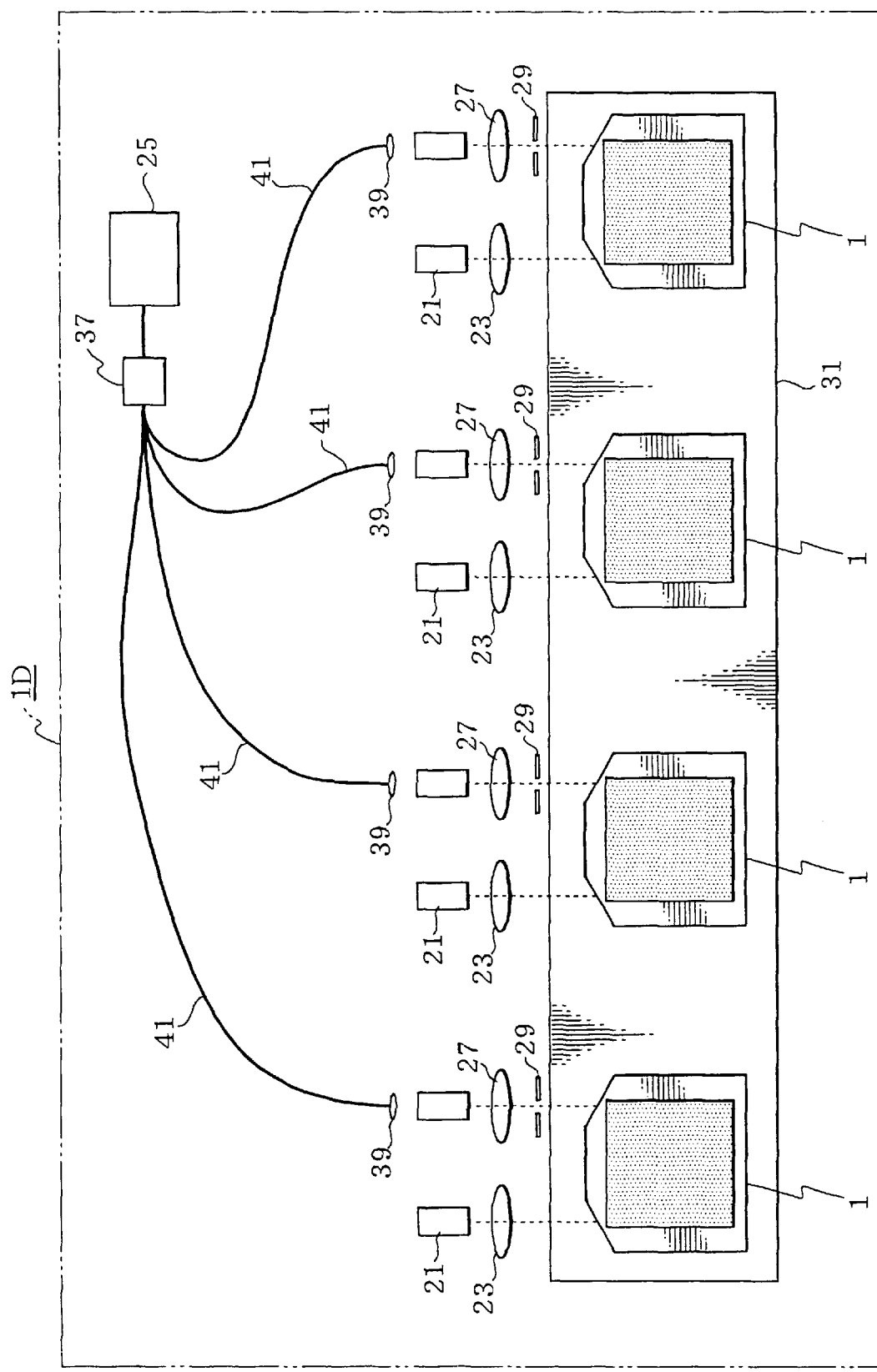
FIG. 12 is a view showing still another example of the immune reaction measuring instrument according to the third embodiment of the present invention.

Next, FIG. 12 shows yet another immune reaction measuring instrument 1D. Like the immune reaction measuring instrument 1C shown in FIG. 11, the immune reaction measuring instrument 1D can carry a plurality of SPR sensor plates 1. The immune reaction measuring instrument 1D is different from the immune reaction measuring instrument 1C in that like the light source 21 and the light detecting means 25, the SPR sensor plates 1 are immovable.

More specifically, the SPR sensor plates 1 are carried on the stage 31. In this embodiment, by way of example, four SPR sensor plates 1 are carried thereon. The SPR sensor plates 1 are linearly arranged at predetermined intervals. The light source 21, the first condenser lens 23, the second condenser lens 27, and the slit 29 are provided correspondingly to each SPR sensor plate 1. Further, a receptacle 39 is arranged near the second condenser lens 27 and opposite to the SPR sensor plate 1. The receptacle 39 receives light condensed by the second condenser lens 27 and then introduces it into an optical fiber 41 connected to the receptacle 39.

The optical fiber 41 connected to the receptacle 39 is connected to an optical-fiber coupler 37. In this embodiment, since the four SPR sensor plates 1 are carried, four optical fibers 41 are collectively connected to the optical-fiber coupler 37. Furthermore, the optical fibers 41 from the optical-fiber coupler 37 are connected to the light detecting means 25 so that light can be introduced into the light detecting means 25.

If the immune reaction measuring instrument 1D is used to carry out immune reaction measurements, a procedure to take is as follows: First, if the light sources 21 are sequentially lighted, a lighting operation control section (not shown) for controlling the lighting operation of the light sources 21 must be provided. Thus, the optical fiber coupler 37 and the light detecting means 25 have only to analyze incident light.

On the other hand, if all the light sources 21 are lighted, the optical fiber coupler 37 must have an optical-switch function to sequentially switch the SPR sensor plates 1. In this case, no lighting operation control section for controlling the lighting of the light sources 21 is required. The numbers of the light sources 21 and the light detecting means 25 are only an example and are not particularly limited.

Fourth Embodiment

Figure 13A:
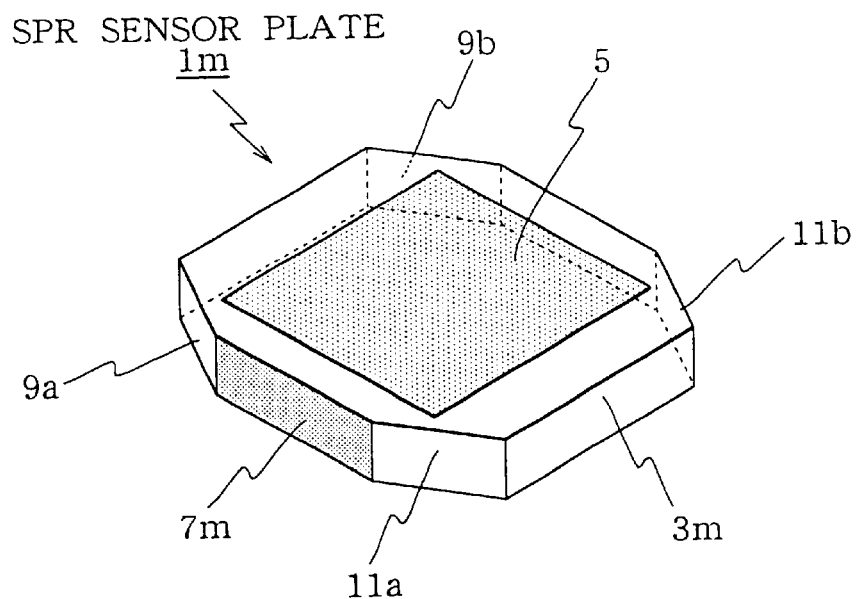
FIG. 13(A) is a general perspective view.

Next, an SPR sensor plate 1m according to a fourth embodiment of the present invention will be described with reference to FIGS. 13 and 14. The SPR sensor plate $1m$ has the same main components as the SPR sensor plate 1 shown in the first embodiment has. The SPR sensor plate $1m$, however, is different from the SPR sensor plate 1 in that two beams are simultaneously introduced into a light waveguide $3m$.

More specifically, the SPR sensor plate $1m$ has light incident surfaces $9a$ and $9b$ and light exit surfaces $11a$ and $11b$. That is, a reflecting metal film $7m$ is not formed all over the end surfaces of the light waveguide $3m$, but inclined surfaces are formed on both ends of each of the end surfaces and the reflecting metal film $7m$ is not formed thereon. The inclined surfaces constitute the incident surfaces $9a$ and $9b$ and the exit surfaces $11a$ and $11b$. Thus, light can be entered into corresponding ones of these portions and emitted from the other portions.

Figure 13B:
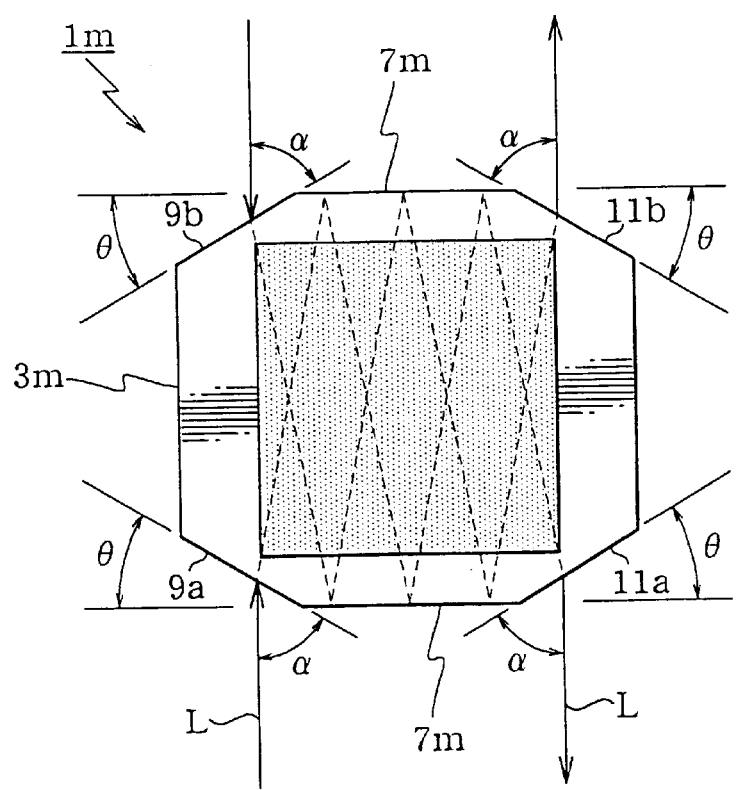
FIG. 13(B) is a top view.
Figure 14:
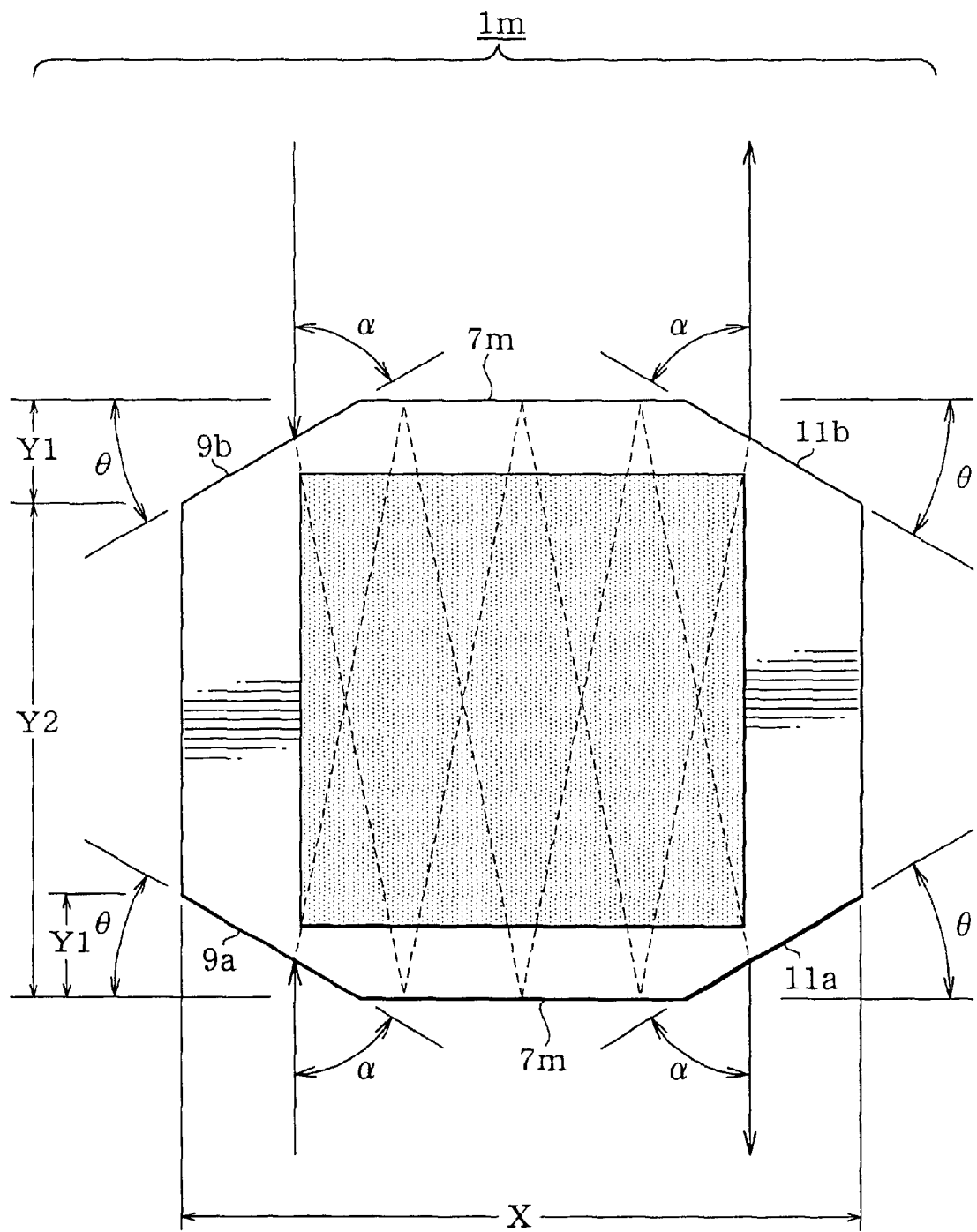
FIG. 14 is a top view useful in explaining dimensions of the SPR sensor plate disclosed in FIG. 13.

As seen in FIG. 13(B), a specific usage of this SPR sensor plate is such that a first beam is allowed to enter the first incident surface $9a$ (lower left of the figure) of the SPR sensor plate $1m$. The first beam is then repeatedly reflected inside the light waveguide $3m$ and then emitted from the first exit surface $11a$ (lower right of the figure). On the other hand, a second beam is incident on the second incident surface $9b$ (upper left of the figure) of the SPR sensor plate $1m$ and is emitted from the second exit surface $11b$ (upper right of the figure).

The use of the SPR sensor plate $1m$ configured as described above enables immune reaction measurements as described below. That is, if the same beams from two lights sources are incident on the SPR sensor plate $1m$, the two beams are simultaneously detected to enable the immune reaction to be measured more sensitively. On the other hand, two points (different immune reactions) can be measured by detecting the distribution of wavelength using different light sources and different light detecting means.

By way of example, the SPR sensor plate $1m$ has such specific dimensions as described below. As shown in FIG. 14, in the width direction of this SPR sensor plate, the length between both ends of the light waveguide $3m$ is defined as X. In addition, in the height direction, the height of the inclined surface is defined as Y1, and the height from an end of the inclined surface to the lower-most end is defined as Y2. The incident angle of light is defined as $\alpha$. Additionally, air has a refractive index of 1. Furthermore, each beam is assumed to be reflected inside the light waveguide 3 $2a-1$ times (reference a denotes a positive real number). The dimensions of the light waveguide 3 are set so as to establish the following equation:

$$X=Y1/(\tan\theta)+\{(2a-1)Y1+(2a)Y2\}\times\tan[\{(\pi/2)-\theta\}-\arc\sin\{1/(n1)\}\times\cos\alpha\}]$$

where $$\theta=\pi/2-\alpha \text{ and } \alpha=2.$$

[Variations]

Next, variations of this embodiment will be described below. References to the drawings are omitted from the description of these variations.

[Variation 4-1]

First, a variation 4-1 of this embodiment will be described. An SPR sensor plate according to the variation 4-1 has the same basic components as the above SPR sensor plate $1m$ has. This variation, however, is different from the SPR sensor plate $1m$ in that the surface on the sensing metal film side is coated with a hydrophobic film. That is, the light waveguide is the same as in the SPR sensor plate $1m$. The peripheral portion of the top surface of the light waveguide except for the portion of the sensing metal film 5 is coated with the hydrophobic film. This hydrophobic film is made of a fluorine-based resin, which repels water; thus, when the subject is injected in the portion of the sensing metal film, it remains therein due to the surface tension of the subject itself.

If the hydrophobic film has a refractive index $n2$, the relationship with the refractive index $n1$ of the light waveguide 3 is $n1>n2$ (total-reflection condition). Since such a refractive index condition is met, light is totally reflected inside the light waveguide to enable correct immune reaction measurements. Various resins, for example, PTFE (Poly Tetra Fluoro Ethylene), FEP (Fluorinated Ethylene Propylene copolymer), PFA (tetra fluoro ethylene-PerFluoro Alkylvinyl ether coploymer), and ETFE (Ethylene Tetra Fluoro Ethylene) may be used for the hydrophobic film. Various processes may be used to form the hydrophobic film, but the spin coat process, the dip coat process, or the roll coat process is desirably used. Alternatively, the hydrophobic film may be formed using the vacuum evaporation process or the like.

[Variation 4-2]

Next, an SPR sensor plate according to a variation 4-2 of this embodiment will be described. This variation is characterized in that a top plate is installed on the top surface (on which the sensing metal film is formed) of the light waveguide. The top plate is composed of glass, plastic, or the like so that if its refractive index is defined as $n3$, the condition $n1>n3$ (total-reflection condition) is met. Thus, light traveling through the light waveguide is totally reflected by the boundary surface between the light waveguide and the top plate to return to the interior of the light waveguide.

Various methods may be used to join the light waveguide and the top plate together. For example, they may be jointed together by means of an adhesive or may be welded together by heating the boundary surface. They may also be stuck together by applying fat and oil to the boundary surface. In this case, the adhesive or the like inserted between the waveguide and the top plate must have a smaller refractive index than that $n1$ of the light waveguide.

The top plate must be shaped to cover the top surface of the light waveguide except for the portion of the sensing metal film. That is, the peripheral portion of the top surface of the light waveguide is covered with the top plate. Accordingly, the portion of the sensing metal film is recessed relative to its peripheries by a distance equal to the thickness of the top plate; the subject is stored in this recess. Thus, even if a larger amount of subject is injected into the recess, the subject is prevented from leaking from the SPR sensor plate. Although the top plate according to this variation has a rectangular through-hole in its central area, the shape of the through-hole is not particularly limited. That is, various shapes may be used so as to correspond to the shape of the sensing metal film.

[4-3]

Next, a variation 4-3 of this embodiment will be described. This variation is characterized in that both the top surface (on which the sensing metal film is formed) and bottom surface of the light waveguide are coated with hydrophobic films. However, the bottom surface of the light waveguide is entirely coated with the hydrophobic film. This is because the sensing metal film is not formed on the bottom surface of the light waveguide. The material of the hydrophobic film is similar to that described above, and for example, PTFE, FEP, PFA, or ETFE may be used.

When the hydrophobic film coated on the bottom surface of the light waveguide has a refractive index n4, the refractive indices of the relevant members must be n1>n2 and n1>n4, or n1>n2=n4. These conditions are required to cause total reflection inside the light waveguide.

[Variation 4-4]

Next, a variation 4-4 of this embodiment will be described. This variation differs from the above variations in that a bottom plate is installed on the bottom surface of the light waveguide. That is, the bottom plate composed of glass or plastic is installed all over the bottom surface of the light waveguide.

When the bottom plate installed on the bottom surface of the light waveguide has a refractive index n5, the refractive indices of the relevant members must be n1>n3 and n1>n5, or n1>n3=n5.

Fifth Embodiment

Next, a fifth embodiment of the present invention will be described with reference to FIGS. 15 and 16. This embodiment has the same basic components as the SPR sensor plate 1m of the above fourth embodiment has. An SPR sensor plate In according to this embodiment, however, is characterized in that the first incident surface 9a and the first exit surface 11a are formed on opposite end surfaces. It is also characterized in that the second incident surface 9b and the second exit surface 11b are formed on opposite surfaces.

Figure 15A:
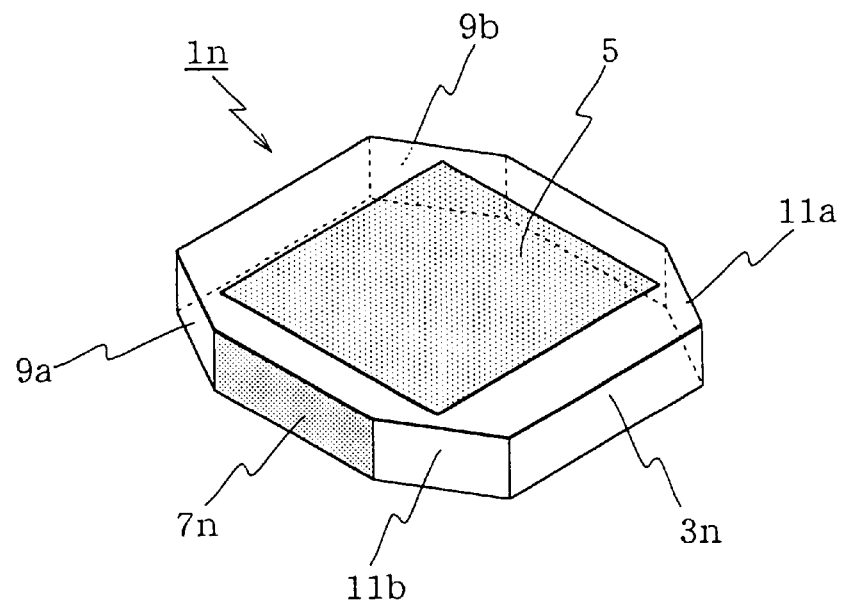
FIG. 15(A) is a general perspective view.
Figure 15B:
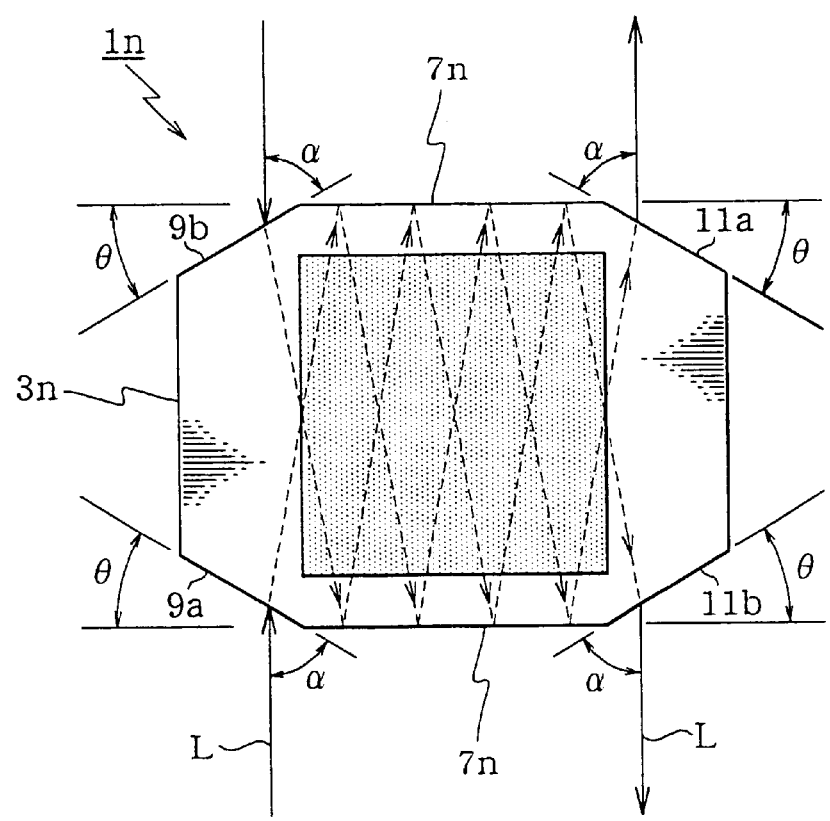
FIG. 15(B) is a top view.
Figure 16:
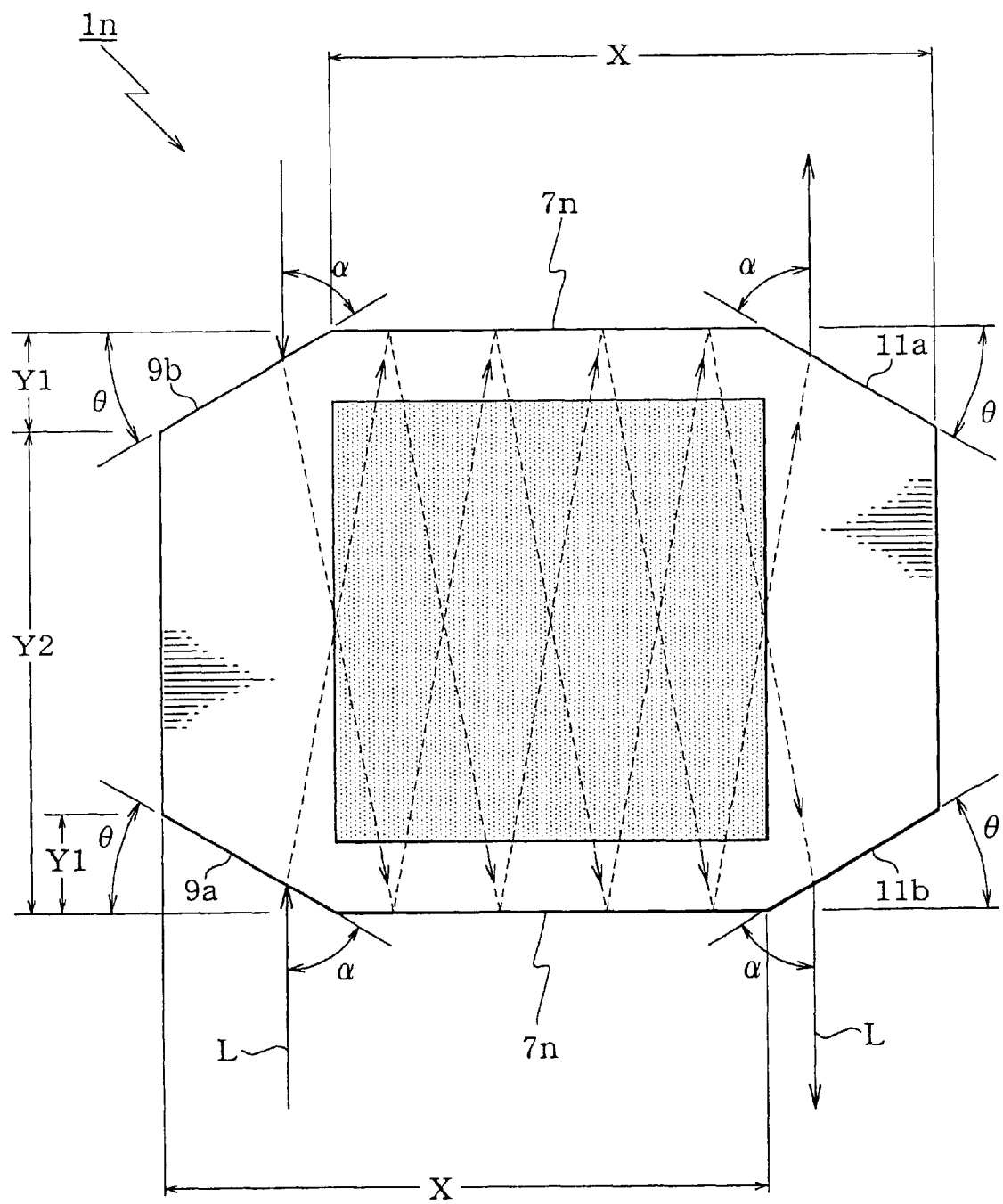
FIG. 16 is a top view useful in explaining dimensions of the SPR sensor plate disclosed in FIG. 15.
Figure 17:
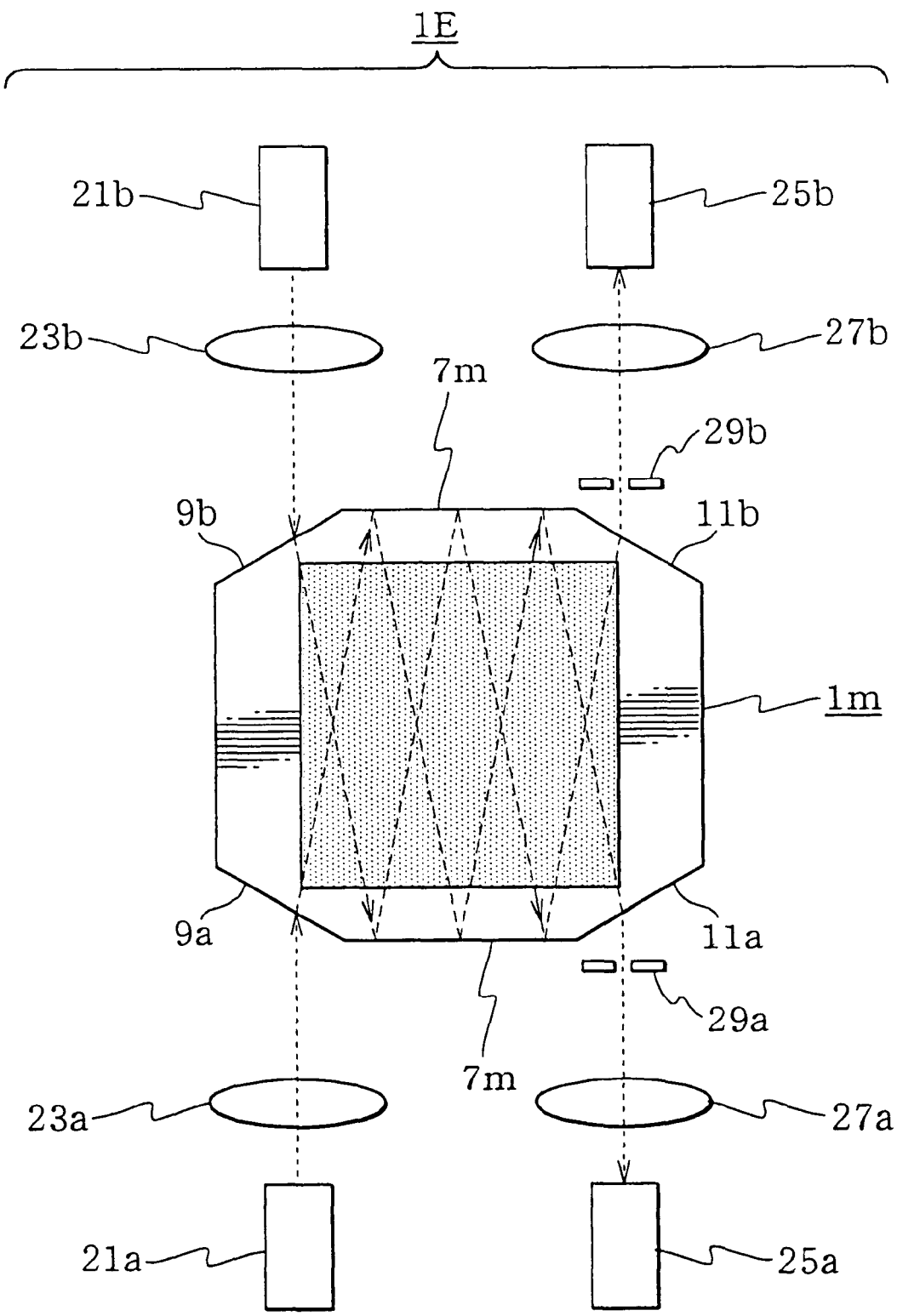
FIG. 17 is a view showing an immune reaction measuring instrument according to a sixth embodiment of the present invention.

Specifically, the SPR sensor plate in shown in FIG. 15 is similar to the SPR sensor plate 1m according to the first embodiment. In the SPR sensor plate in of this embodiment, the first light incident surface 9a is located closer to the reader (in FIG. 15(B), in its lower left), while the first exit surface 11a is located further from the reader (in FIG. 15(B), in its upper right). The second light incident surface 9b is located further from the reader (in FIG. 15 (B), in its upper left), while the second exit surface 11b is located closer to the reader (in FIG. 15(B), in its lower right).

Specific dimensions of this SPR sensor plate will be shown below by way of example. That is, as shown in FIG. 16, in the width direction of this SPR sensor plate, the length from an end of the light waveguide 3n to an end of an inclined surface thereof is defined as X. In the height direction, the height of the inclined surface is defined as Y1, and the height from an end of the inclined surface to the lower-most portion of the light waveguide 3n is defined as Y2. The incident angle of light is defined as α. In addition, air has a refractive index of 1. Furthermore, light is assumed to be reflected inside the light waveguide 3 2a times (reference a denotes a positive real number). Then, the dimensions of the light waveguide 3n are set so as to establish the following equation:

$$X=\{(2a)Y1+(2a+1)Y2\}\times\tan[\{(\pi/2)-\theta\}-\arcsin\{(1/(n1))\times\cos\alpha\}]$$

where $\theta=\pi/2-\alpha$ and a=2.

Beams La and Lb entering the light waveguide 3n from the incident surfaces 9a and 9b are repeatedly reflected inside the light waveguide 3n and then emitted from the exit surfaces 11a and 11b, respectively, on the opposite end surface. In the meantime, each beam is reflected four times by the boundary surface between the light waveguide 3n and a reflecting metal film 7n. The beams are emitted from the exit surfaces 11a and 11b at the angle α, which is also measured on incidence.

When the incident surfaces 9a and 9b are thus formed on one side of the light waveguide 3n, whereas the exit surfaces 11a and 11b are formed on the other side, many types of immune reactions can be simultaneously measured.

[Variations]

Next, variations of the fifth embodiment will be described below. References to the drawings are omitted from the description of these variations.

[Variation 5-1]

First, a variation 5-1 of this embodiment will be described. An SPR sensor plate according to this variation has the same basic components as the above SPR sensor plate 1n has. This variation, however, is different from the SPR sensor plate 1n in that the surface on the sensing metal film side is coated with a hydrophobic film. That is, the light waveguide is the same as in the SPR sensor plate 1n. The peripheral portion of the top surface of the light waveguide except for the portion of the sensing metal film is coated with the hydrophobic film. This hydrophobic film is made of a fluorine-based resin, which repels water; thus, when the subject is injected in the portion of the sensing metal film, it remains therein due to the surface tension of the subject itself.

If the hydrophobic film has a refractive index n2, the relationship with the refractive index n1 of the light waveguide is n1>n2 (total-reflection condition). Since such a refractive index condition is met, light is totally reflected inside the light waveguide to enable correct immune reaction measurements. Various resins, for example, PTFE (Poly Tetra Fluoro Ethylene), FEP (Fluorinated Ethylene Propylene copolymer), PFA (tetra fluoro ethylene-PerFluoro Alkylvinyl ether coploymer), and ETFE (Ethylene Tetra Fluoro Ethylene) may be used for the hydrophobic film. Various processes may be used to form the hydrophobic film, but the spin coat process, the dip coat process, or the roll coat process is desirably used. Alternatively, the hydrophobic film may be formed using the vacuum evaporation process or the like.

[Variation 5-2]

Next, an SPR sensor plate according to a variation 5-2 of this embodiment will be described. This variation is characterized in that a top plate is installed on the top surface (on which the sensing metal film is formed) of the light waveguide. The top plate is composed of glass, plastic, or the like so that if its refractive index is defined as n3, the condition n1>n3 (total-reflection condition) is met. Thus, light traveling through the light waveguide is totally reflected by the boundary surface between the light waveguide and the top plate to return to the interior of the light waveguide.

Various methods may be used to join the light waveguide and the top plate together. For example, they may be jointed together by means of an adhesive or may be welded together by heating the boundary surface. They may also be stuck together by applying fat and oil to the boundary surface. In this case, the adhesive or the like inserted between the waveguide and the top plate must have a smaller refractive index than that n1 of the light waveguide.

The top plate must be shaped to cover the top surface of the light waveguide except for the portion of the sensing metal film. That is, the peripheral portion of the top surface of the light waveguide is covered with the top plate. Accordingly, the portion of the sensing metal film is recessed relative to its peripheries by a distance equal to the thickness of the top plate; the subject is stored in this recess. Thus, even if a larger amount of subject is injected into the recess, the subject is prevented from leaking from the SPR sensor plate. Although the top plate according to this variation has a rectangular through-hole in its central area, the shape of the through-hole is not particularly limited. That is, various shapes may be used so as to correspond to the shape of the sensing metal film.

[Variation 5-3]

Next, a variation 5-3 of this embodiment will be described. This variation is characterized in that both the top surface (on which the sensing metal film is formed) and bottom surface of the light waveguide are coated with hydrophobic films. However, the bottom surface of the light waveguide is entirely coated with the hydrophobic film. This is because the sensing metal film is not formed on the bottom surface of the light waveguide. The material of the hydrophobic film is similar to that described above, and for example, PTFE, FEP, PFA, or ETFE may be used.

When the hydrophobic film coated on the bottom surface of the light waveguide has a refractive index n4, the refractive indices of the relevant members must be n1>n2 and n1>n4, or n1>n2=n4. These conditions are required to cause total reflection inside the light waveguide.

[Variation 5-4]

Next, a variation 5-4 of this embodiment will be described. This variation differs from the above variations in that a bottom plate is installed on the bottom surface of the light waveguide. That is, the bottom plate composed of glass or plastic is installed all over the bottom surface of the light waveguide.

When the bottom plate installed on the bottom surface of the light waveguide has a refractive index n5, the refractive indices of the relevant members must be n1>n3 and n1>n5, or n1>n3=n5.

Sixth Embodiment

Next, a sixth embodiment of the present invention will be described with reference to FIGS. 17 to 21. An immune reaction measuring instrument 1E, shown in FIG. 17, uses the SPR sensor plate 1m described in the fourth embodiment. The immune reaction measuring instrument 1E comprises two sets of light sources 21a and 21b for applying predetermined beams, first condenser lenses 23a and 23b for condensing the beams from the light sources 21a and 21b, respectively, second condenser lenses 27a and 27b for condensing the beams emitted from the exit surfaces 11a and 11b, light detecting means 25a and 25b for receiving the beams condensed by the second condenser lenses 27a and 27b, respectively, and slits 29a and 29b arranged between the SPR sensor plate 1m and the second condenser lenses 27a and 27b.

The light sources 21a and 21b apply beams L of predetermined wavelength bands; specifically, it comprises a white LED lamp. In this embodiment, the distribution of the wavelengths of beams passing through the SPR sensor plate 1m is analyzed before and after immune reaction to thereby measure the immune reaction. Accordingly, the light sources 21a and 21b desirably apply beams having stable wavelength distributions. Commercially available white LED lamps apply light of a wavelength band between about 450 and 750 nm. The light sources 21a and 21b may be different from the above white LED lamp as long as they can apply light of a certain wavelength band. Specifically, the light sources 21a and 21b may be halogen lamps. Moreover, they are similar to those described in the third embodiment.

Next, the light detecting means 25a and 25b will be described. The light detecting means 25a and 25b used to measure the distributions of wavelengths comprises two sets of spectroscopes. Alternatively, they may be photodiodes. The light detecting means 25a and 25b are similar to those described in the third embodiment.

Figure 18:
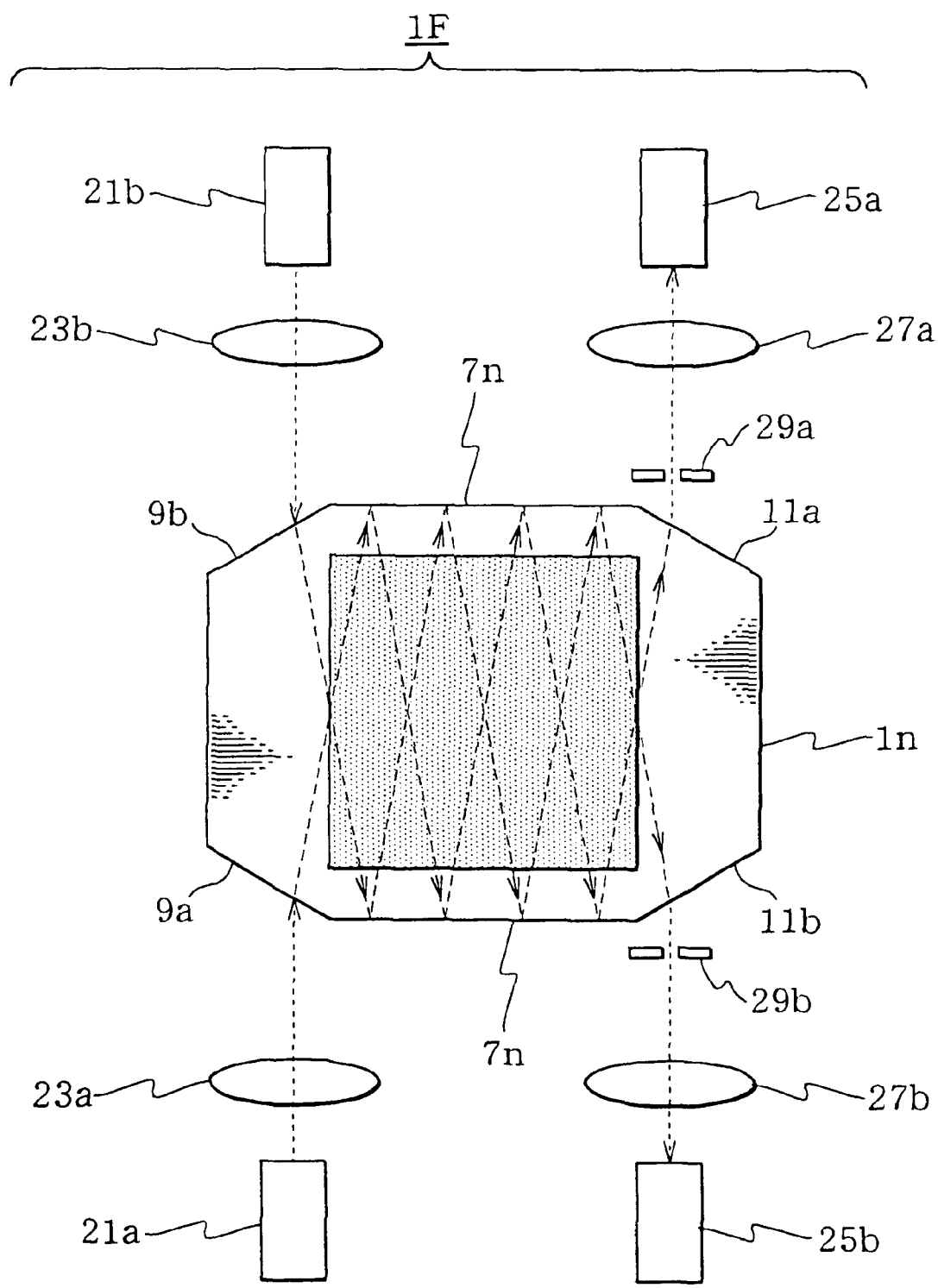
FIG. 18 is a view showing another example of the immune reaction measuring instrument according to the sixth embodiment of the present invention.

FIG. 18 shows an immune reaction measuring instrument 1F employing the SPR sensor plate in according to the fourth embodiment. This instrument is similar to the above immune reaction measuring instrument 1E except that the incident surface 9a and the corresponding exit surface 11a are formed on opposite end surfaces of the light waveguide. The incident surface 9b and the corresponding exit surface 11b are also formed on opposite surfaces.

Figure 19:
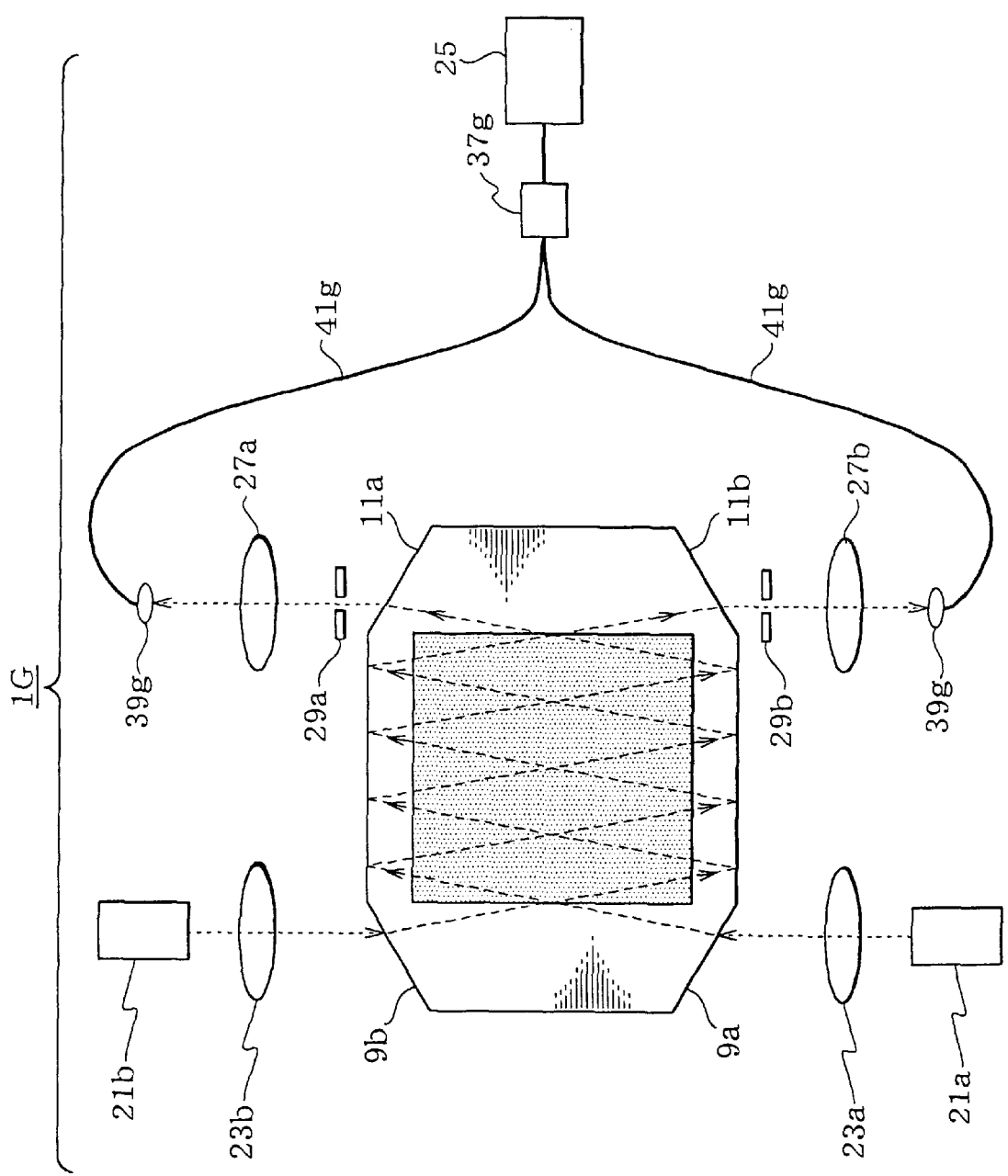
FIG. 19 is a view showing yet another example of the immune reaction measuring instrument according to the sixth embodiment of the present invention.

FIG. 19 shows the immune reaction measuring instrument 1F shown in FIG. 18 comprising only one light detecting means 25. Specifically, a receptacle 39g is disposed near each of the second condenser lenses 27a and 27b. An optical fiber 41g is connected to each receptacle 39g. These two optical fibers 41g are connected to an optical fiber coupler 37g. An optical fiber is extended from the optical fiber coupler 37g and finally connected to the light detecting means 25.

When the optical fibers 41g are used to introduce light into the light detecting means 25, this measuring instrument requires only one light detecting means 25. Further, when the optical fiber coupler 37g has an optical-path switching function, many types of immune reactions can be simultaneously measured. In contrast, when the same light source is used to simultaneously detect beams from two optical paths, the immune reaction can be measured more sensitively.

Figure 20:
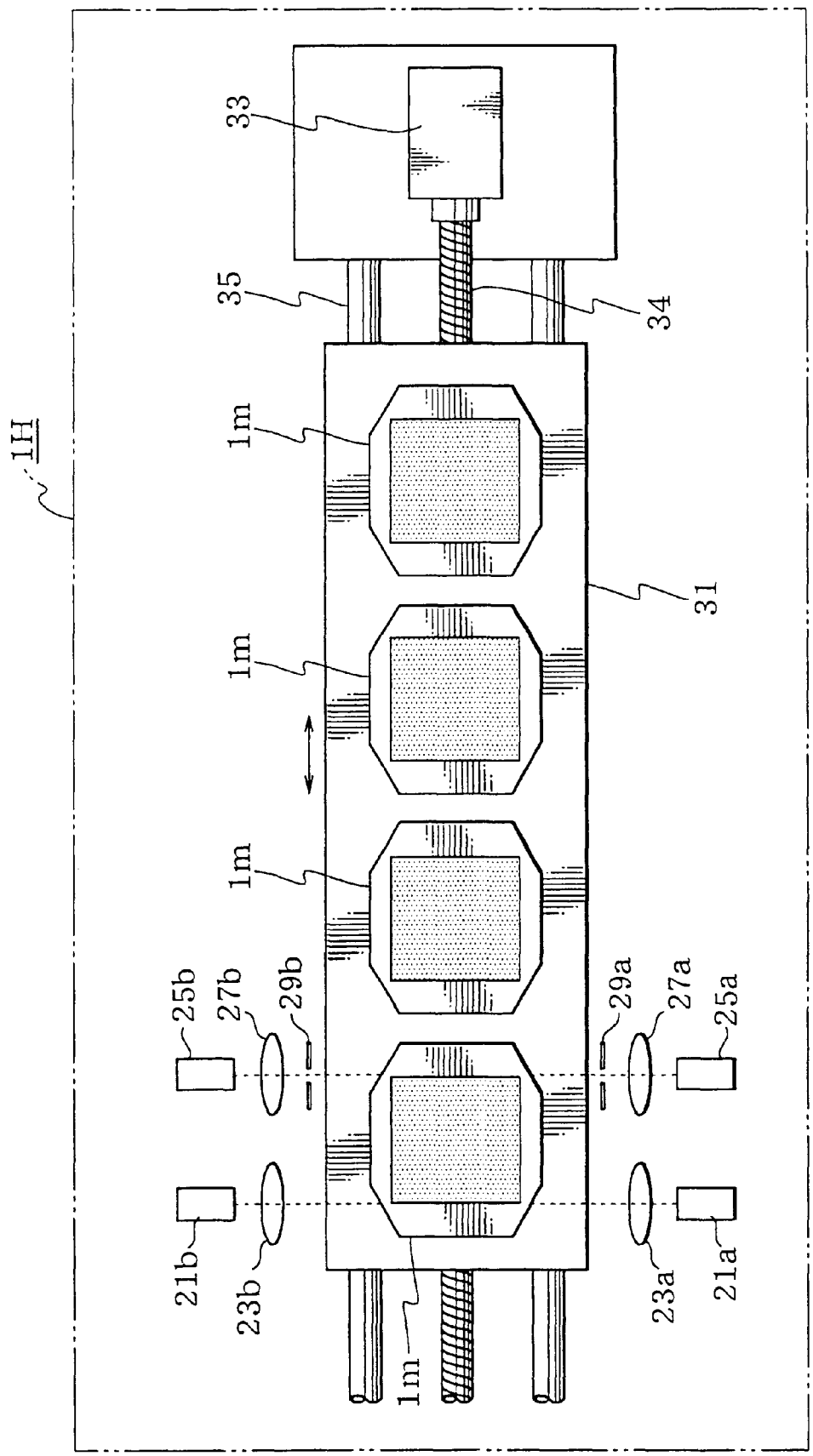
FIG. 20 is a view showing still another example of the immune reaction measuring instrument according to the sixth embodiment of the present invention.

FIG. 20 is a top view showing an immune reaction measuring instrument 1H in which a plurality of SPR sensor plates 1m can be installed. The immune reaction measuring instrument 1H carries the SPR sensor plates 1m on a stage 31 that is movable. The stage 31 is moved by means of a screw 34 and a monitor 33 rotating the screw 34.

More specifically, the stage 31 is slidably fixed to two guide shafts 35 so as to movable along them. The stage 31 has an external thread (not shown) formed in the bottom surface thereof and on which the screw 34 is fitted. Thus, as the motor 33 is rotated, the screw 34 rotates. As the screw 34 rotates, the stage 31 moves along the guide shafts 35. In this case, if the motor 33 is a stepping motor, the stage 31 can be positioned accurately.

On the other hand, neither the light sources 21a and 21b nor the light detecting means 25a and 25b nor the condenser lenses 23a and 23b and 27a and 27b move. That is, the movement of the stage 31 allows the switching of the SPR sensor plates 1m for immune reaction measurements. Thus, neither the light sources 21a and 21b nor the light detecting means 25a and 25b require any complicated movement means.

Figure 21:
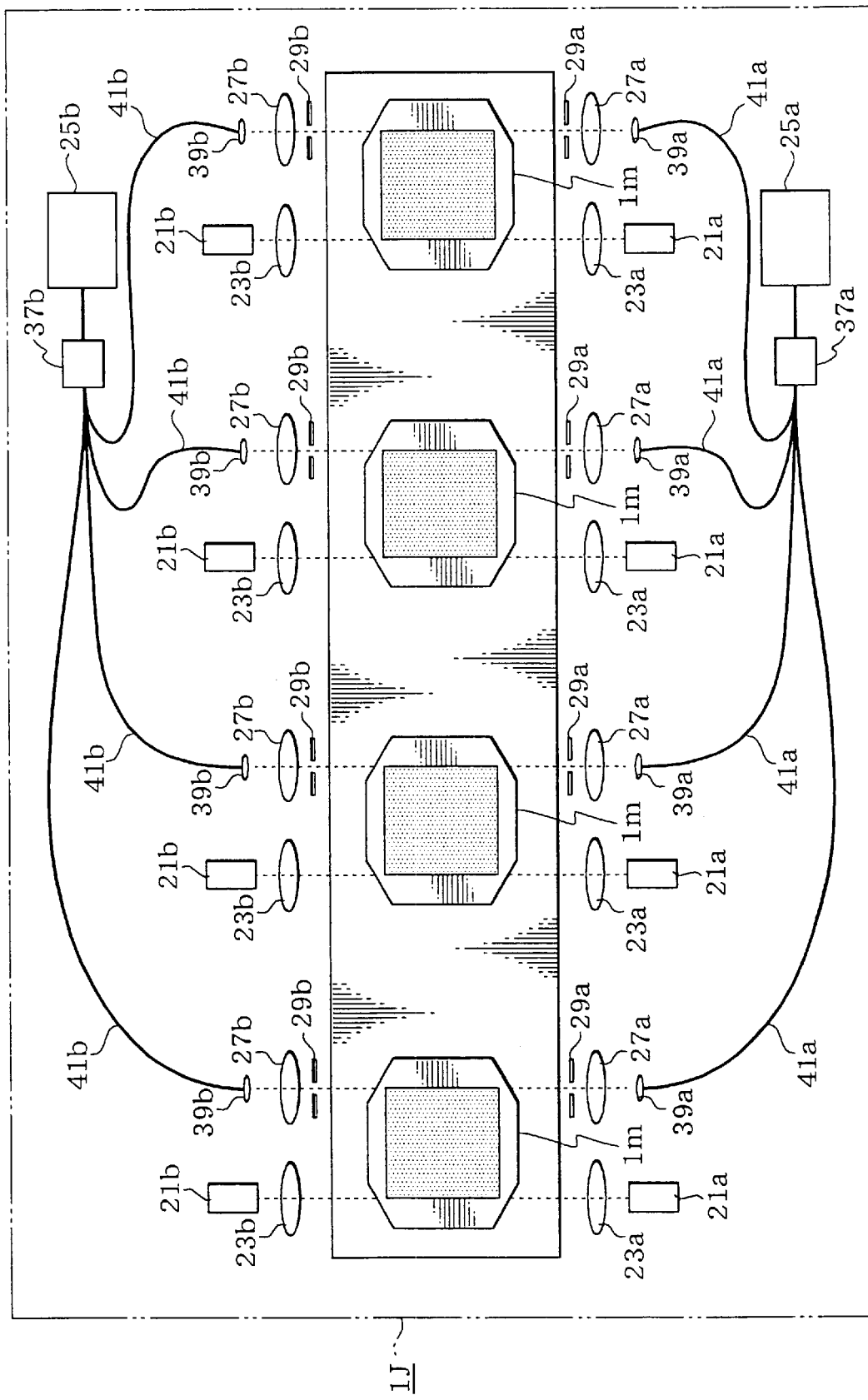
FIG. 21 is a view showing still another example of the immune reaction measuring instrument according to the sixth embodiment of the present invention.

Next, FIG. 21 shows yet another immune reaction measuring instrument 1J. Like the immune reaction measuring instrument 1H shown in FIG. 20, the immune reaction measuring instrument 1J can carry a plurality of SPR sensor plates 1m. The immune reaction measuring instrument 1J is different from the immune reaction measuring instrument 1H in that like the light sources 21a and 21b and the light detecting means 25a and 25b, the SPR sensor plates 1m are immovable.

More specifically, the SPR sensor plates 1m are carried on the stage 31j. In this embodiment, by way of example, four SPR sensor plates 1m are carried thereon. The SPR sensor plates 1m are linearly arranged at predetermined intervals. The light sources 21a and 21b, the first condenser lenses 23a and 23b, the second condenser lenses 27a and 27b, and the slits 29a and 29b are provided correspondingly to each SPR sensor plate 1m. Further, receptacles 39a and 39b are arranged near the second condenser lenses 27a and 27b, respectively, and opposite to the SPR sensor plate 1m. The receptacles 39a and 39b receive beams condensed by the second condenser lenses 27a and 27b, respectively, and then introduce them into optical fibers 41a and 41b connected to the receptacles 39a and 39b, respectively.

The optical fibers 41a and 41b connected to the receptacles 39a and 39b, respectively, are connected to optical-fiber couplers 37a and 37b. In this embodiment, since the four SPR sensor plates 1m are carried, four optical fibers 41a and 41b are collectively connected to the optical-fiber coupler 37a and 37b. Furthermore, optical fibers from the optical-fiber couplers 41a and 41b connected to the light detecting means 25a and 25b so that beams can be introduced into the light detecting means 25a and 25b.

One of the effects of the present invention is that since light is transmitted through the light waveguide while being reflected inside it, it is reflected by the sensing film member more often than in the prior art, thereby allowing a predetermined sensitivity to be maintained even if the size of the SPR sensor plate is reduced. Accordingly, the SPR sensor plate may be compact. In addition, if this SPR sensor plate is used to configure an immune reaction measuring instrument, the entire instrument will be compact. Consequently, the manufacturing costs of the SPR sensor plate or the immune reaction measuring instrument can be reduced.

Further, since the light waveguide used for the SPR sensor plate is shaped like a plate, the sensing metal film can be formed easily to thereby allow a dielectric film and an antibody (or antigen) to be bound easily. Additionally, since the size of the sensing metal film can be reduced, the thickness of the metal film becomes more uniform to improve the measurement sensitivity.

Another effect of the present invention is that at least one of the incident and exit surfaces of the light waveguide constitutes an inclined surface of a predetermined inclination, enabling the optical axes of the light source, the light detecting means, and the like to be designed easily. In particular, when a plurality of inclined surfaces have the same inclination, the optical axes of the light source and the light detecting means may be parallel with each other. As a result, the optical system can be designed easily and set more accurately, thereby allowing immune reaction to be measured more accurately.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2000-210024 (Filed on Jul. 11, 2000) including specification, claims, drawings and summary are incorporated herein by reference in its entirety.

What is claimed is:

1. An SPR sensor plate, comprising:
   an optical waveguide for allowing light from a light source to pass therethrough; and a sensing metal film formed on part of a surface of the optical waveguide,
   wherein said optical waveguide has reflecting metal films formed on opposite end surfaces thereof except for a light incident surface and a light exit surface, and
   at least one of said incident surface and exit surface is, inclined through a predetermined inclination.

2. The SPR sensor plate according to claim 1, further comprising at least two sets of said incident surface and exit surface.

3. The SPR sensor plate according to claim 1, wherein said incident surface and exit surface are formed on a same end surface side.

4. The SPR sensor plate according to claim 1, wherein said incident surface and exit surface are formed on different end surface sides.

5. The SPR sensor plate according to claim 1, wherein said incident surface and exit surface are inclined, and said inclined surfaces have a same inclination.

6. The SPR sensor plate according to claim 1, wherein said reflecting metal films are parallel with one another.

7. The SPR sensor plate according to claim 1, wherein said sensing metal film is formed of Au, Ag, or Ni.

8. The SPR sensor plate according to claim 7, wherein said sensing metal film is formed in said optical waveguide via a Cr film.

9. The SPR sensor plate according to claim 1, wherein said reflecting metal film is formed of Au, Ag, or Al.

10. The SPR sensor plate according to claim 1, wherein a hydrophobic film is formed around said sensing metal film constituting a part of the surface of said optical waveguide.

11. The SPR sensor plate according to claim 10, wherein said hydrophobic film is a fluorine-based resin film.

12. An immune reaction measuring instrument including an SPR sensor plate according to claim 1.

13. The immune reaction measuring instrument according to claim 12, comprising at least two of said SPR sensor plates.

* * * * *

UNITED STATES PATENT AND TRADEMARK OFFICE
CERTIFICATE OF CORRECTION

PATENT NO. : 6,507,402 B2
DATED : January 14, 2003
INVENTOR(S) : M. Negami et al.

It is certified that error appears in the above-identified patent and that said Letters Patent is hereby corrected as shown below:

<u>Column 20,</u>
Line 17, after "is" delete ",".

Signed and Sealed this

Fourteenth Day of October, 2003

JAMES E. ROGAN
*Director of the United States Patent and Trademark Office*